(12) United States Patent
Buchter-Larsen et al.

(10) Patent No.: US 6,914,175 B2
(45) Date of Patent: Jul. 5, 2005

(54) PROCESS FOR PREPARING AN ANTI-OXIDANT

(75) Inventors: Aksel Buchter-Larsen, Copenhagen (DK); Ian Marcussen, Copenhagen (DK)

(73) Assignee: BioLogic A/S, Frederiksberg (DK)

( * ) Notice: Subject to any disclaimer, the term of this patent is extended or adjusted under 35 U.S.C. 154(b) by 0 days.

(21) Appl. No.: 09/423,126

(22) Filed: Nov. 5, 1999

(65) Prior Publication Data

US 2002/0170083 A1 Nov. 14, 2002

Related U.S. Application Data

(63) Continuation of application No. PCT/IB98/00708, filed on May 6, 1998.

(30) Foreign Application Priority Data

May 6, 1997 (GB) .............................................. 9709161

(51) Int. Cl.[7] ........................ C12N 15/00; C12N 15/52; C12N 15/82; A01H 1/00; A01H 5/00
(52) U.S. Cl. .................... 800/317.2; 800/288; 800/298; 536/23.1; 536/23.2; 426/590; 426/592
(58) Field of Search .............................. 800/288, 317.2, 800/200, 205, 298; 536/23.2, 23.1; 426/590, 592; 435/6; 485/468

(56) References Cited

U.S. PATENT DOCUMENTS 5,695,970 A    12/1997  Yu et al.
5,780,709 A  * 7/1998  Adams et al. .............. 800/205
6,013,504 A  * 1/2000  Yu et al. ..................... 435/232

FOREIGN PATENT DOCUMENTS

| GB | 2 296 243 A |   | 4/1995 |         |
|----|-------------|---|--------|---------|
| GB | 2 297 090 A |   | 4/1995 |         |
| GB | 2294048 A   |   | 4/1996 |         |
| WO | WO 94/09122 | * | 4/1994 | 530/300 |
| WO | WO 95/10616 |   | 4/1995 |         |
| WO | WO 95/10617 |   | 4/1995 |         |
| WO | WO 95/10618 |   | 4/1995 |         |
| WO | WO 96/12026 |   | 4/1996 |         |
| WO | 97/04113    | * | 2/1997 |         |

OTHER PUBLICATIONS

Ishida et al, Nature Biotechnology, vol. 14, pp 745–850, Jun. 1996.*
Perl et al, Nature Biotechnology, vol. 14, pp 624–628, May 1996.*
Enriqueta R. Guinto et al, Unexpected crucial role of residue 225 in serine proteases, Proc. Natl. Acad. Sci. USA, vol. 96, pp. 1852–1857, Mar. 1999.*
Avihai Perl et al, Establishment of an Agrobacterium–mediated transformation system for grape (Vitis Vinifera L.): The role of antioxidants during grape–Agrobacterium interactions, Nature Biotechnology vol. 14, May 1996.*
Lilia Alberghina, Protein Engineering In Industrial Biotechnology, Jan. 2001.*
Bernard R. Glick et al, Molecular Biotechnology Principles and Applications, of recombinant DNA, Jul. 1995.*
Tsuneo Nakamura et al., (1986) J. Biochem,, "Oxidation of 1,5–Anhydro–D–Glucitol to 1,5–Anhydro–D–Fructose Catalyzed by an Enzyme from Bacterial Membranes". vol. 99, 607–613.
Marie–Antoinette Baute, et al. (1988) Phytochemistry "Fungal Enzymic Activity Degrading 1.4–α–D–Glucans to 1.5–D–Anhydrofructose" vol. 27(11),pp. 3401–3403.
Shukun Yu et al., Planta(1993), "α–1,4–Glucan lyase, a new class of starch/glycogen–degrading enzyme" vol. 191:137–142.
Shukun Yu, et al. Biochimica et Biophysica Acta, (1993), "α–1,4–Glucan lyase, a new class of starch/glycogen degrading enzyme, I. Efficient purification and characterization from red seaweeds" vol. 1156,No. 3, pp. 313–320.
Shunichi Kametani, et al. Eru. J. Biochem. (1996), "Hepatic production of 1,5–anhydrofructose and 1,5–anhydroglucitol in rat by the third glycogenolytic pathway" vol. 242, pp. 832–838.

* cited by examiner

*Primary Examiner*—Amy J. Nelson
*Assistant Examiner*—Russell Kallis
(74) *Attorney, Agent, or Firm*—Frommer Lawrence & Haug; Thomas J. Kowalski; Anne-Marie Yvon

(57) ABSTRACT

A process for preparing an anti-oxidant in a plant is described. The process comprises transforming a plant with a nucleic acid encoding glucan lyase thereby producing the anti-oxidant anhydrofructose in situ.

27 Claims, No Drawings

PROCESS FOR PREPARING AN ANTI-OXIDANT

CROSS-REFERENCE TO RELATED APPLICATIONS

This application is a continuation of PCT application PCT/IB98/00708 filed May 6, 1998 designating the U.S., which claims priority from Great Britain Patent Application 9709161.5 filed May 6, 1997.

The present invention relates to a process of preparing an anti-oxidant.

An anti-oxidant prevents, inhibits or reduces the oxidation rate of an oxidisable medium. In particular, anti-oxidants are used for the preservation of food, especially when the food is or comprises a fat. Typical chemical anti-oxidants include aromatic amines, substituted phenols and sulphur compounds. Examples of anti-oxidants for food products are polyvinylpolypyrrolidone, dithiothreitol, sulphur dioxide, synthetic γ-tocopherol, δ-tocopherol, L-ascorbic acid, sodium L-ascorbate, calcium L-ascorbate, ascorbyl palmitate, propyl gallate, octyl gallate, dodecyl gallate, lecithin, diphenylamine ethoxyquin and butylated hydroxytoluene. Two commonly used anti-oxidants are GRINDOX 142 (obtained from Danisco A/S) and GRINDOX 1029 (obtained from Danisco A/S).

Typically, anti-oxidants are added to foodstuffs, such as beverages.

For example, anti-oxidants are used in the preparation of alcoholic beverages such as beer, cider, ale etc. In particular, there is a wide spread use of anti-oxidants in the preparation of wine. In this regard, Butzke and Bisson in Agro-Food-Industry Hi-Tech (July/August 1996 pages 26–30) present a review of wine manufacture.

According to Butzke and Bisson (ibid):

"Wine is the product of the natural fermentation of grape must or juice. In the case of red wine, the skins are present during the initial fermentation to allow extraction of pigment and important flavour and aroma constituents from the skin. The term "must" refers to the crushed whole grapes. In the case of white wine production, skins are removed prior to fermentation and only the juice is retained and processed. . . .

Grapes are harvested and brought directly to the winery from the field. The grapes are then crushed at the winery and the must either transferred to a tank for fermentation (red wine) or pressed to separate juice from the skin and seeds (white wine). In this latter case, the juice is then transferred to a tank for fermentation. The tanks may either be inoculated with a commercial wine strain of Saccharomyces or allowed to undergo a natural or uninoculated fermentation. In a natural fermentation, Saccharomyces cells are greatly outnumbered by wild (non-Saccharomyces) yeast and bacteria at the beginning of fermentation. By the end of the fermentation Saccharomyces is the dominant and most often only organism isolateable. Inoculation with a commercial wine strain or with fermenting juice or must changes the initial ratio of the numbers of different microorganisms, allowing Saccharomyces to dominate the fermentation much earlier.

The metabolic activity of microorganisms in wine results in the production of aroma and flavour compounds some of which are highly objectionable to the consumer and all of which are distinct from the compounds responsible for the varietal character of the wine. . . .

Sulphur dioxide addition prevents chemical oxidation reactions and in this sense is an important stabilizer of the natural grape aroma and flavour. It may be added to the must or juice to preserve flavour, not necessarily as an antimicrobial agent. However, its antimicrobial activity must be considered when choosing a strain to be genetically modified for wine production."

Hence, potentially harmful chemicals—such as sulphur dioxide—are used in wine manufacture.

The present invention seeks to overcome any problems associated with the prior art methods of preparing foodstuffs with antioxidants.

According to a first aspect of the present invention there is provided a process of preparing a medium that comprises an anti-oxidant and at least one other component, the process comprising preparing in situ in the medium the anti-oxidant; and wherein the anti-oxidant is prepared from a glucan by use of recombinant DNA techniques.

According to a second aspect of the present invention there is provided a process of preparing a medium that comprises an anti-oxidant and at least one other component, the process comprising preparing in situ in the medium the anti-oxidant; and wherein the anti-oxidant is prepared by use of a recombinant glucan lyase.

According to a third aspect of the present invention there is provided a medium prepared by the process according to the present invention.

Other aspects of the present invention include:

Use of anhydrofructose as an anti-oxidant for a medium comprising at least one other component, wherein the anhydrofructose is prepared in situ in the medium.

Use of anhydrofructose as a means for imparting or improving stress tolerance in a plant, wherein the anhydrofructose is prepared in situ in the plant.

Use of anhydrofructose as a means for imparting or improving the transformation of a grape, wherein the anhydrofructose is prepared in situ in the grape.

Use of anhydrofructose as a means for increasing anti-oxidant levels in a foodstuff (preferably a fruit or vegetable, more preferably a fresh fruit or a fresh vegetable), wherein the anhydrofructose is prepared in situ in the foodstuff.

Use of anhydrofructose as a pharmaceutical in a foodstuff, wherein the anhydrofructose is prepared in situ in the foodstuff.

A method of administering a foodstuff comprising anhydrofructose, wherein the anhydrofructose is in a pharmaceutically acceptable amount and acts as a pharmaceutical; and wherein the anhydrofructose has been prepared in situ in the foodstuff.

Use of anhydrofructose as a nutraceutical in a foodstuff, wherein the anhydrofructose is prepared in situ in the foodstuff.

A method of administering a foodstuff comprising anhydrofructose, wherein the anhydrofructose is in a nutraceutically acceptable amount and acts as a nutraceutical; and wherein the anhydrofructose has been prepared in situ in the foodstuff.

Use of glucan lyase as a means for imparting or improving stress tolerance in a plant, wherein the glucan lyase is prepared in situ in the plant.

Use of glucan lyase as a means for imparting or improving the transformation of a grape, wherein the glucan lyase is prepared in situ in the grape.

Use of glucan lyase as a means for increasing antioxidant levels in a foodstuff (preferably a fruit or vegetable, more preferably a fresh fruit or a fresh vegetable), wherein the glucan lyase is prepared in situ in the foodstuff.

Use of glucan lyase in the preparation of a pharmaceutical in a foodstuff, wherein the glucan lyase is prepared in situ in the foodstuff.

A method of administering a foodstuff comprising an antioxidant, wherein the antioxidant is in a pharmaceutically acceptable amount and acts as a pharmaceutical; and wherein the antioxidant has been prepared in situ in the foodstuff from a glucan lyase.

Use of glucan lyase in the preparation of a nutraceutical in a foodstuff, wherein the glucan lyase is prepared in situ in the foodstuff.

A method of administering a foodstuff comprising an antioxidant, wherein the antioxidant is in a nutraceutically acceptable amount and acts as a nutraceutical; and wherein the antioxidant has been prepared in situ in the foodstuff from a glucan lyase.

Use of a nucleotide sequence coding for a glucan lyase as a means for imparting or improving stress tolerance in a plant, wherein the nucleotide sequence is expressed in situ in the plant.

Use of a nucleotide sequence coding for a glucan lyase as a means for imparting or improving the transformation of a grape, wherein the nucleotide sequence is expressed in situ in the grape.

Use of a nucleotide sequence coding for a glucan lyase as a means for increasing antioxidant levels in a foodstuff (preferably a fruit or vegetable, more preferably a fresh fruit or a fresh vegetable), wherein the nucleotide sequence is expressed in situ in the foodstuff.

Use of a nucleotide sequence coding for a glucan lyase as a means for creating a pharmaceutical in a foodstuff, wherein the nucleotide sequence is expressed in situ in the foodstuff.

A method of administering a foodstuff comprising an antioxidant, wherein the antioxidant is in a pharmaceutically acceptable amount and acts as a pharmaceutical; and wherein the antioxidant has been prepared in situ in the foodstuff by means of a nucleotide sequence coding for a glucan lyase.

Use of a nucleotide sequence coding for a glucan lyase as a means for creating a nutraceutical in a foodstuff, wherein the nucleotide sequence is expressed in situ in the foodstuff.

A method of administering a foodstuff comprising an antioxidant, wherein the antioxidant is in a nutraceutically acceptable amount and acts as a nutraceutical; and wherein the antioxidant has been prepared in situ in the foodstuff by means of a nucleotide sequence coding for a glucan lyase.

The term "nutraceutical" means a compound that is capable of acting as a nutrient (i.e. it is suitable for, for example, oral administration) as well as being capable of exhibiting a pharmaceutical effect and/or cosmetic effect.

In contrast to the usual practice of adding anti-oxidants media, such as foodstuffs, we have now found that particular anti-oxidants can be prepared in situ in the medium.

The in situ preparation of anti-oxidants is particularly advantageous in that less, or even no, additional anti-oxidants need be added to the medium, such as a food product.

The present invention is also believed to be advantageous as it provides a means of improving stress tolerance of plants.

The present invention is also advantageous as it provides a means for viably transforming grape.

The present invention is further advantageous in that it enables the levels of antioxidants in foodstuffs to be elevated. This may have beneficial health implications. In this regard, recent reports (e.g. Biotechnology Newswatch Apr. 21 1997 "*Potent Antioxidants, as strong as those in fruit, found in coffee*" by Marjorie Shaffer) suggest that antioxidants have a pharmaceutical benefit, for example in preventing or suppressing cancer formation.

General in situ preparation of antioxidants in plants has been previously reviewed by Badiani et al in Agro-Food-Industry Hi-Tech (March/April 1996 pages 21–26). It is to be noted, however, that this review does not mention preparing in situ antioxidants from a glucan, let alone by use of a recombinant glucan lyase.

Preferably, the glucan comprises α-1,4 links.

Preferably, the glucan is starch or a unit of starch.

Preferably, the glucan is a substrate for a recombinant enzyme such that contact of the glucan with the recombinant enzyme yields the anti-oxidant.

Preferably, the enzyme is a glucan lyase.

Preferably, the enzyme is an α-1,4-glucan lyase.

Preferably, the enzyme comprises any one of the sequences shown as SEQ ID Nos 1–6, or a variant, homologue or fragment thereof.

Preferably, the enzyme is any one of the sequences shown as SEQ ID Nos 1–6.

Preferably, the enzyme is encoded by a nucleotide sequence comprising any one of the sequences shown as SEQ ID Nos 7–12, or a variant, homologue or fragment thereof.

Preferably, the enzyme is encoded by a nucleotide sequence having any one of the sequences shown as SEQ ID Nos 7–12.

Preferably, the anti-oxidant is anhydrofructose.

Preferably, the anti-oxidant is 1,5-D-anhydrofructose.

Preferably, the medium is, or is used in the preparation of, a foodstuff.

Preferably, the foodstuff is a beverage.

Preferably, the beverage is an alcoholic beverage.

Preferably, the beverage is a wine.

Preferably, the anti-oxidant is prepared in situ in the component and is then released into the medium.

Preferably, the component is a plant or a part thereof.

Preferably, the component is all or part of a cereal or a fruit.

Preferably, the component is all or part of a grape.

The medium may be used as or in the preparation of a foodstuff, which includes beverages. In the alternative, the medium may be for use in polymer chemistry. In this regard, the in situ generated anti-oxidants could therefore act as oxygen scavengers during, for example, the synthesis of polymers, such as the synthesis of bio-degradable plastic.

In accordance with the present invention, the anti-oxidant (preferably anhydrofructose) is prepared in situ in the medium. In other words, the antioxidant (preferably anhydrofructose) that is prepared in situ in the medium is used as an anti-oxidant in the medium. In one emdodiment, the antioxidant (preferably anhydrofructose) that is prepared in situ in the medium is used as the main anti-oxidant in the medium.

The term "in situ in the medium" as used herein includes the anti-oxidant being prepared by action of a recombinant enzyme expressed by the component on a glucan—which glucan is a substrate for the enzyme. The term also includes the anti-oxidant being prepared by action of a recombinant enzyme expressed by the component on a glucan—which glucan is a substrate for the enzyme—within the component and the subsequent generation of the anti-oxidant. The term also includes the recombinant enzyme being expressed by the component and then being released into the medium, which enzyme acts on a glucan—which glucan is a substrate for the enzyme—present in the medium to form the anti-oxidant in the medium. The term also covers the presence or addition of another component to the medium, which component then expresses a recombinant nucleotide sequence which results in exposure of part or all of the medium to an anti-oxidant, which anti-oxidant may be a recombinant enzyme or a recombinant protein expressed and released by the other component, or it may be a product of a glucan—which glucan is a substrate for the enzyme—within the medium that has been exposed to the recombinant enzyme or the recombinant protein.

The term "by use of recombinant DNA techniques" as used herein includes the anti-oxidant being any obtained by use of a recombinant enzyme or a recombinant protein, which enzyme or protein acts on the glucan. The term also includes the anti-oxidant being any obtained by use of an enzyme or protein, which enzyme or protein acts on a recombinant glucan.

The term "starch" in relation to the present invention includes native starch, degraded starch, modified starch, including its components amylose and amylopectin, and the glucose units thereof.

The terms "variant", "homologue" or "fragment" in relation to the enzyme include any substitution of, variation of, modification of, replacement of, deletion of or addition of one (or more) amino acid from or to the sequence providing the resultant amino acid sequence has α-glucan lyase activity, preferably having at least the same activity of any one of the enzymes shown as SEQ ID No. 1–6. In particular, the term "homologue" covers homology with respect to structure and/or function providing the resultant enzyme has α-glucan lyase activity. With respect to sequence homology, preferably there is at least 75%, more preferably at least 85%, more preferably at least 90% homology to any one of the sequences shown as SEQ ID No.s 1–6. More preferably there is at least 95%, more preferably at least 98%, homology to any one of the sequences shown as SEQ ID No. 1–6.

The terms "variant", "homologue" or "fragment" in relation to the nucleotide sequence coding for the enzyme include any substitution of, variation of, modification of, replacement of, deletion of or addition of one (or more) nucleic acid from or to the sequence providing the resultant nucleotide sequence codes for an enzyme having α-glucan lyase activity, preferably having at least the same activity of any one of the enzymes shown as SEQ ID No. 1–6. In particular, the term "homologue" covers homology with respect to structure and/or function providing the resultant nucleotide sequence codes for an enzyme having α-glucan lyase activity. With respect to sequence homology, preferably there is at least 75%, more preferably at least 85%, more preferably at least 90% homology to any one of the sequences shown as SEQ ID No. 7–12. More preferably there is at least 95%, more preferably at least 98%, homology to any one of the sequences shown as SEQ ID No. 7–12.

The above terms are synonymous with allelic variations of the sequences.

The present invention also covers nucleotide sequences that can hybridise to the nucleotide sequence of the present invention.

The term "nucleotide" in relation to the present invention includes cDNA.

According to the present invention there is therefore provided a method of preparing in situ in an oxidisable medium an anti-oxidant. In a preferred embodiment, the anti-oxidant is anhydrofructose, more preferably 1,5-D-anhydrofructose. 1,5-D-anhydrofructose has been chemically synthesised (Lichtenthaler in Tetrahedron Letters Vol 21 pp 1429–1432). 1,5-D-anhydrofructose is further discussed in WO 95/10616, WO 95/10618 and GB-B-2294048.

The main advantages of using 1,5-D-anhydrofructose as an anti-oxidant are that it is a natural product, it is non-metabolisable, it is easy to manufacture, it is water-soluble, and it is generally non-toxic.

According to WO 95/10616, WO 95/10618 and GB-B-2294048, 1,5-D-anhydrofructose may be prepared by the enzymatic modification of substrates based on α-1,4-glucan by use of the enzyme α-1,4-glucan lyase. A typical α-1,4-glucan based substrate is starch.

Today, starches have found wide uses in industry mainly because they are cheap raw materials. There are many references in the art to starch. For example, starch is discussed by Salisbury and Ross in Plant Physiology (Fourth Edition, 1991, Published by Wadsworth Publishing Company—especially section 11.7). In short, however, starch is one of the principal energy reserves of plants. It is often found in colourless plastids (amyloplasts), in storage tissue and in the stroma of chloroplasts in many plants. Starch is a polysaccharide carbohydrate. It comprises two main components: amylose and/or amylopectin. Both amylose and/or amylopectin consist of straight chains of α(1, 4)-linked glucose units (ie glycosyl residues) but in addition amylopectin includes α(1,6) branched glucose units.

Some of the glucan lyases discussed in WO 95/10616 and WO 95/10618 that are suitable for producing 1,5-D-anhydrofructose from starch are shown as SEQ I.D. No.s 1–4. Some of the glucan lyases discussed in GB-B-2294048 that are suitable for producing 1,5-D-anhydrofructose from starch are shown as SEQ I.D. No.s 5–6.

Some of the nucleotide sequences coding for glucan lyases discussed in WO 95/10616 and WO 95/10618 that are suitable for producing 1,5-D-anhydrofructose from starch are shown as SEQ I.D. No.s 7–10. Some of the nucleotide sequences coding for glucan lyases discussed in GB-B-2294048 that are suitable for producing 1,5-D-anhydrofructose from starch are shown as SEQ I.D. No.s 11–12.

A further glucan lyase is discussed in WO 94/09122.

The recombinant nucleotide sequences coding for the enzyme may be cloned from sources such as a fungus, preferably *Morchella costata* or *Morchella vulgaris*, or from a fungally infected algae, preferably *Gracilariopsis lemaneiformis*, or from algae lone, preferably *Gracilariopsis lemaneiformis*.

In a preferred embodiment, the 1,5-D-anhydrofructose is prepared in situ by treating an α-1,4-glucan with a recombinant α-1,4-glucan lyase, such as any one of those presented as SEQ I.D. No.s 1–6.

Detailed commentary on how to prepare the enzymes shown as sequences SEQ I.D. No.s 1–6 may be found in the teachings of WO 95/10616, WO 95/10618 and GB-B-2294048. Likewise, detailed commentary on how to isolate and clone the nucleotide sequences SEQ I.D. No.s 7–12 may be found in the teachings of WO 95/10616, WO 95/10618 and GB-B-2294048.

If the glucan contains links other than and in addition to the α-1,4- links the recombinant α-1,4-glucan lyase can be used in conjunction with a suitable reagent that can break the other links—such as a recombinant hydrolase—preferably a recombinant glucanohydrolase.

General teachings of recombinant DNA techniques may be found in Sambrook, J., Fritsch, E. F., Maniatis T. (Editors) Molecular Cloning. A laboratory manual. Second edition. Cold Spring Harbour Laboratory Press. New York 1989.

In order to express a nucleotide sequence, the host organism can be a prokaryotic or a eukaryotic organism. Examples of suitable prokaryotic hosts include *E. coli* and *Bacillus subtilis*. Teachings on the transformation of prokaryotic hosts is well documented in the art, for example see Sambrook et al (Molecular Cloning: A Laboratory Manual, 2nd edition, 1989, Cold Spring Harbor Laboratory Press). If a prokaryotic host is used then the gene may need to be suitably modified before transformation—such as by removal of introns.

In one embodiment, the host organism can be of the genus Aspergillus, such as *Aspergillus niger*. A transgenic Aspergillus can be prepared by following the teachings of Rambosek, J. and Leach, J. 1987 (Recombinant DNA in filamentous fungi: Progress and Prospects. CRC Crit. Rev. Biotechnol. 6:357–393), Davis R. W. 1994 (Heterologous gene expression and protein secretion in Aspergillus. In: Martinelli S. D., Kinghorn J. R. (Editors) Aspergillus: 50 years on. Progress in industrial microbiology vol 29. Elsevier Amsterdam 1994. pp 525–560), Ballance, D. J. 1991 (Transformation systems for Filamentous Fungi and an Overview of Fungal Gene structure. In: Leong, S. A., Berka R. M. (Editors) Molecular Industrial Mycology. Systems and Applications for Filamentous Fungi. Marcel Dekker Inc. New York 1991, pp 1–29) and Turner G. 1994 (Vectors for genetic manipulation. In: Martinelli S. D., Kinghorn J. R.(Editors) Aspergillus: 50 years on. Progress in industrial microbiology vol 29. Elsevier Amsterdam 1994. pp. 641–666). However, the following commentary provides a summary of those teachings for producing transgenic Aspergillus.

For almost a century, filamentous fungi have been widely used in many types of industry for the production of organic compounds and enzymes. For example, traditional japanese koji and soy fermentations have used Aspergillus sp. Also, in this century *Aspergillus niger* has been used for production of organic acids particular citric acid and for production of various enzymes for use in industry.

There are two major reasons why filamentous fungi have been so widely used in industry. First filamentous fungi can produce high amounts of extracelluar products, for example enzymes and organic compounds such as antibiotics or organic acids. Second filamentous fungi can grow on low cost substrates such as grains, bran, beet pulp etc. The same reasons have made filamentous fungi attractive organisms as hosts for heterologous expression of recombinant enzymes according to the present invention.

In order to prepare the transgenic Aspergillus, expression constructs are prepared by inserting a requisite nucleotide sequence into a construct designed for expression in filamentous fungi.

Several types of constructs used for heterologous expression have been developed. These constructs can contain a promoter which is active in fungi. Examples of promoters include a fungal promoter for a highly expressed extracelluar enzyme, such as the glucoamylase promoter or the α-amylase promoter. The nucleotide sequence can be fused to a signal sequence which directs the protein encoded by the nucleotide sequence to be secreted. Usually a signal sequence of fungal origin is used. A terminator active in fungi ends the expression system.

Another type of expression system has been developed in fungi where the nucleotide sequence can be fused to a smaller or a larger part of a fungal gene encoding a stable protein. This can stabilize the protein encoded by the nucleotide sequence. In such a system a cleavage site, recognized by a specific protease, can be introduced between the fungal protein and the protein encoded by the nucleotide sequence, so the produced fusion protein can be cleaved at this position by the specific protease thus liberating the protein encoded by the nucleotide sequence. By way of example, one can introduce a site which is recognized by a KEX-2 like peptidase found in at least some Aspergilli. Such a fusion leads to cleavage in vivo resulting in protection of the expressed product and not a larger fusion protein.

Heterologous expression in Aspergillus has been reported for several genes coding for bacterial, fungal, vertebrate and plant proteins. The proteins can be deposited intracellularly if the nucleotide sequence is not fused to a signal sequence. Such proteins will accumulate in the cytoplasm and will usually not be glycosylated which can be an advantage for some bacterial proteins. If the nucleotide sequence is equipped with a signal sequence the protein will accumulate extracelluarly.

With regard to product stability and host strain modifications, some heterologous proteins are not very stable when they are secreted into the culture fluid of fungi. Most fungi produce several extracelluar proteases which degrade heterologous proteins. To avoid this problem special fungal strains with reduced protease production have been used as host for heterologous production.

For the transformation of filamentous fungi, several transformation protocols have been developed for many filamentous fungi (Ballance 1991, ibid). Many of them are based on preparation of protoplasts and introduction of DNA into the protoplasts using PEG and $Ca^{2+}$ ions. The transformed protoplasts then regenerate and the transformed fungi are selected using various selective markers. Among the markers used for transformation are a number of auxotrophic markers such as argB, trpC, niaD and pyrG, antibiotic resistance markers such as benomyl resistance, hygromycin resistance and phleomycin resistance. A commonly used transformation marker is the amdS gene of *A. nidulans* which in high copy number allows the fungus to grow with acrylamide as the sole nitrogen source.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al (1987, Yeast Biotechnology, D R Berry et al, eds, pp 401–429, Allen and Unwin, London) and by King et al (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe E Kenny (1993, "Yeast as a vehicle for the expression of heterologous genes", Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic Saccharomyces, expression constructs are prepared by inserting the nucleotide sequence into a construct designed for expression in yeast. Several types of constructs used for heterologous expression have been developed. The constructs contain a promoter active in yeast fused to the nucleotide sequence, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic Saccharomyces can be prepared by following the teachings of Hinnen et al (1978, Proceedings of the National Academy of Sciences of the USA 75, 1929); Beggs, J D (1978, Nature, London, 275, 104); and Ito, H et al (1983, J Bacteriology 153, 163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, eg G418.

Another host organism is a plant. In this regard, the art is replete with references for preparing transgenic plants. Two documents that provide some background commentary on the types of techniques that may be employed to prepare transgenic plants are EP-B-0470145 and CA-A-2006454—some of which commentary is presented below.

The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech March/April 1994 17–27).

Thus, in one aspect, the present invention relates to a vector system which carries a recombinant nucleotide sequence and which is capable of introducing the nucleotide sequence into the genome of an organism, such as a plant, and wherein the nucleotide sequence is capable of preparing in situ an anti-oxidant.

The vector system may comprise one vector, but it can comprise at least two vectors. In the case of two vectors, the vector system is normally referred to as a binary vector system. Binary vector systems are described in further detail in Gynheung An et al. (1980), Binary Vectors, *Plant Molecular Biology Manual* A3, 1–19.

One extensively employed system for transformation of plant cells with a given promoter or nucleotide sequence or construct is based on the use of a Ti plasmid from *Agrobacterium tumefaciens* or a Ri plasmid from *Agrobacterium rhizogenes* (An et al. (1986), *Plant Physiol.* 81, 301–305 and Butcher D. N. et al. (1980), *Tissue Culture Methods for Plant Pathologists*, eds.: D. S. Ingrams and J. P. Helgeson, 203–208).

Several different Ti and Ri plasmids have been constructed which are suitable for the construction of the plant or plant cell constructs described above.

The nucleotide sequence of the present invention should preferably be inserted into the Ti-plasmid between the border sequences of the T-DNA or adjacent a T-DNA sequence so as to avoid disruption of the sequences immediately surrounding the T-DNA borders, as at least one of these regions appear to be essential for insertion of modified T-DNA into the plant genome.

As will be understood from the above explanation, if the organism is a plant, then the vector system of the present invention is preferably one which contains the sequences necessary to infect the plant (e.g. the vir region) and at least one border part of a T-DNA sequence, the border part being located on the same vector as the genetic construct. Preferably, the vector system is an *Agrobacterium tumefaciens* Ti-plasmid or an *Agrobacterium rhizogenes* Ri-plasmid or a derivative thereof, as these plasmids are well-known and widely employed in the construction of transgenic plants, many vector systems exist which are based on these plasmids or derivatives thereof.

In the construction of a transgenic plant the nucleotide sequence or construct or vector of the present invention may be first constructed in a microorganism in which the vector can replicate and which is easy to manipulate before insertion into the plant. An example of a useful microorganism is *E. coli.*, but other microorganisms having the above properties may be used. When a vector of a vector system as defined above has been constructed in *E. coli.* it is transferred, if necessary, into a suitable Agrobacterium strain, e.g. *Agrobacterium tumefaciens*. The Ti-plasmid harbouring the first nucleotide sequence or construct of the invention is thus preferably transferred into a suitable Agrobacterium strain, e.g. *A. tumefaciens*, so as to obtain an Agrobacterium cell harbouring the promoter or nucleotide sequence or construct of the invention, which DNA is subsequently transferred into the plant cell to be modified.

As reported in CA-A-2006454, a large number of cloning vectors are available which contain a replication system in *E. coli* and a marker which allows a selection of the transformed cells. The vectors contain for example pBR322, the pUC series, the M13 mp series, pACYC 184 etc. In this way, the promoter or nucleotide or construct of the present invention can be introduced into a suitable restriction position in the vector. The contained plasmid is used for the transformation in *E.coli*. The *E. coli* cells are cultivated in a suitable nutrient medium and then harvested and lysed. The plasmid is then recovered and then analysed—such as by any one or more of the following techniques: sequence analysis, restriction analysis, electrophoresis and further biochemical-molecular biological methods. After each manipulation, the used DNA sequence can be restricted or selectively amplified by PCR techniques and connected with the next DNA sequence. Each sequence can be cloned in the same or different plasmid.

After each introduction method of the nucleotide sequence or construct or vector according to the present invention in the plants the presence and/or insertion of further DNA sequences may be necessary. If, for example, for the transformation the Ti- or Ri-plasmid of the plant cells is used, at least the right boundary and often however the right and the left boundary of the Ti- and Ri-plasmid T-DNA, as flanking areas of the introduced genes, can be connected. The use of T-DNA for the transformation of plant cells has been intensively studied and is described in EP-A-120516; Hoekema, in: The Binary Plant Vector System Offset-drukkerij Kanters B. B., Alblasserdam, 1985, Chapter V; Fraley, et al., Crit. Rev. Plant Sci., 4:1–46; and An et al., EMBO J. (1985) 4:277–284.

Direct infection of plant tissues by Agrobacterium is a simple technique which has been widely employed and which is described in Butcher D. N. et al. (1980), *Tissue Culture Methods for Plant Pathologists*, eds.: D. S. Ingrams and J. P. Helgeson, 203–208. For further teachings on this topic see Potrykus (Annu Rev Plant Physiol Plant Mol Biol [1991] 42:205–225) and Christou (Agro-Food-Industry Hi-Tech March/April 1994 17–27). With this technique, infection of a plant may be done on a certain part or tissue of the plant, i.e. on a part of a leaf, a root, a stem or another part of the plant.

Typically, with direct infection of plant tissues by Agrobacterium carrying the first nucleotide sequence or the construct, a plant to be infected is wounded, e.g. by cutting the plant with a razor or puncturing the plant with a needle or rubbing the plant with an abrasive. The wound is then inoculated with the Agrobacterium. The inoculated plant or plant part is then grown on a suitable culture medium.

When plant cells are constructed, these cells are grown and, optionally, maintained in a medium according to the present invention following well-known tissue culturing methods—such as by culturing the cells in a suitable culture medium supplied with the necessary growth factors such as amino acids, plant hormones, vitamins, etc, but wherein the culture medium comprises a component according to the present invention. Regeneration of the transformed cells into genetically modified plants may be accomplished using known methods for the regeneration of plants from cell or tissue cultures, for example by selecting the transformed shoots and by subculturing the shoots on a medium containing the appropriate nutrients, plant hormones, etc.

Further teachings on plant transformation may be found in EP-A-0449375.

Reference may even be made to Spngstad et al (1995 Plant Cell Tissue Organ Culture 40 pp 1–15) as these authors present a general overview on transgenic plant construction.

In one embodiment, the plant is a grapevine. There are a number of teachings in the art on how to prepare transformed grapevines. For example, reference may be made to Baribault et al (J Exp Bot 41 (229) 1990 1045–1050), Baribault et al (Plant Cell Rep 8 (3) 1989 137–140), Scorza et al (J Am Soc Horticultural Science 121 (4) 1996 616–619), Kikkert et al (Plant Cell Reports 15 (5) 1996 311–316), Golles et al (Acta Hortic 1997 vol 447 Number: Horticultural Biotechnology in Vitro Culture and Breeding Pages 265–275), Gray and Scorza (WO-A-97/49277) and Simon Robinson et al (Conference abstracts and paper presented in Biotechnology—Food and Health for the 21st Century, Adelaide, Australia, 1998). By way of example Robinson et al (ibid) disclose a method for transforming grapevine wherein somatic embryos are induced on callus formed from another tissue and Agrobacterium infection is used to transfer target genes into the embryo tissue.

Further reference may be made to the teachings of Andrew Walker in Nature Biotechnology (Vol 14, May 1996, page 582) who states that:

"The grape, one of the most important fruit plants in the world, has been difficult to engineer because of its high levels of tannins and phenols, which interfere with cell culture and transformation; the compounds oxidize quickly and promote the decay of grape cells."

In that same edition of Nature Biotechnology, Perl et al (pages 624–628) report on the use of the combination of polyvinylpolypyrrolidone and dithiothreitol to improve the viability of grape transformation during Agrobacterium infection.

Hence, the present invention provides an alternative means for transforming grape. In this regard, the antioxidant that is prepared in situ by a grape transformed in accordance with the present invention improves the viability of grape transformation during Agrobacterium infection.

Thus, according to one aspect of the present invention, there is provided the use of an antioxidant prepared in situ in order to effectively transform a grape.

In some instances, it is desirable for the recombinant enzyme or protein to be easily secreted into the medium to act as or to generate an anti-oxidant therein. In such cases, the DNA encoding the recombinant enzyme is fused to inter alia an appropriate signal sequence, an appropriate promoter and an appropriate terminator from the chosen host.

For example, for expression in *Aspergillus niger* the gpdA (from the Glyceraldehyde-3-phosphate dehydrogenase gene of *Aspergillus nidulans*) promoter and signal sequence is fused to the 5' end of the DNA encoding the mature lyase. The terminator sequence from the *A. niger* trpC gene is placed 3' to the gene (Punt, P. J. et al 1991—(1991): J. Biotech. 17, 19–34). This construction is inserted into a vector containing a replication origin and selection origin for *E. coli* and a selection marker for *A. niger*. Examples of selection markers for *A. niger* are the amdS gene, the argB gene, the pyrG gene, the hygB gene, the BmlR gene which all have been used for selection of transformants. This plasmid can be transformed into *A. niger* and the mature lyase can be recovered from the culture medium of the transformants. Eventually the construction could be transformed into a protease deficient strain to reduce the proteolytic degradation of the lyase in the medium (Archer D. B. et al 1992—Biotechnol. Lett. 14, 357–362).

In addition, and as indicated above, aside from using *Aspergillus niger* as the host, there are other industrial important microorganisms which could be used as expression systems. Examples of these other hosts include: *Aspergillus oryzae*, Aspergillus sp., Trichoderma sp., *Saccharomyces cerevisiae*, Kluyveromyces sp., Hansenula sp., Pichia sp., *Bacillus subtilis, B. amyloliquefaciens*, Bacillus sp., Streptomyces sp. or *E. coli*.

In accordance with the present invention, a suitable marker or selection means may be introduced into the host that is to be transformed with the nucleotide sequence. Examples of suitable markers or selection means are described in any one of WO-A-93/05163, WO-A-94/20627, GB patent application No. 9702591.0 (filed 7, Feb. 1997), GB patent application No. 9702576.1 (filed 7, Feb. 1997), GB patent application No. 9702539.9 (filed 7, Feb. 1997), GB patent application No. 9702510.0 (filed 7, Feb. 1997) and GB patent application No. 9702592.8 (filed 7 Feb. 1997).

In summation, the present invention relates to a process comprising preparing a medium that comprises an anti-oxidant and at least one other component, the process comprising preparing in situ in the medium the anti-oxidant; and wherein the anti-oxidant is prepared from a glucan by use of recombinant DNA techniques and/or the anti-oxidant is prepared by use of a recombinant glucan lyase.

In a preferred embodiment, the present invention relates to a process a process of preparing a medium that comprises an anti-oxidant and at least one other component, the process comprising preparing in situ in the medium the anti-oxidant; and wherein the anti-oxidant is prepared from a glucan by use of a recombinant glucan lyase.

In a more preferred embodiment, the present invention relates to a process of preparing a medium that comprises an anti-oxidant and at least one other component, the process comprising preparing in situ in the medium the anti-oxidant; wherein the anti-oxidant is prepared from a glucan by use of a recombinant glucan lyase; and wherein the anti-oxidant is anhydro-fructose.

The present invention will now be described only by way of example.

Transgenic Grape

Transformed grapes are prepared following the teachings of Perl et al (ibid) but wherein the use of the combination of polyvinylpolypyrrolidone and dithiothreitol is optional. In these studies, the grapes are transformed with any one of the nucleotide sequences presented as SEQ ID No. 7–12. The transformation leads to in situ preparation of 1,5-D-anhydrofructose. The transformed grapes are beneficial for one or more of the reasons mentioned earlier.

Details on these studies are as follows.

Tissue-Culture Systems for Transformation Studies

The long term somatic embryogenic callus culture is developed from the vegetative tissues of anthers of *Vitis vinifera* CV Superior Seedless. Methods for another culture, induction of somatic embryogenesis and maintenance of embryogenic cultures, are previously described (Perl et al, 1995, Plant Sci 104: 193–200). Briefly, embryogenic calli are maintained on solidified (0.25% gelrite) MS medium (Murashige and Skoog, 1962, Physiol Plant 15: 473–497) supplemented with 6% sucrose, 2 mg/L 2,4-diclorophenoxyacetic acid (2,4-D), 5 mg/L Indole-3-aspartic acid (IASP), 0.2 mg/L 6-benzyladenine (BAP) and 1 mg/L abscisic acid (ABA). Proembryogenic calli are induced by transferring the calli to MS medium supplemented with the same phytohormones, but 2,4-D is substituted with 2 mg/L 2-naphthoxyacetic acid (NOA). This stage is used for transformation experiments.

Agrobacterium Strains

For studying the sensitivity of grape embryogenic calli to the presence of different Agrobacterium strains, or for stable transformation experiments, cocultivation is attempted using the following *A tumefaciens* strains: EHA 101-p492 (Perl et al. 1993, Bio/Technology 11:715–718); LBA 4404-pGPTV (Becker et al, 1992, Plant Mol Biol 20: 1195–1197); and GVE 3101-pPCV91 (Vancanneyt et al, 1990, Mol Gen Genet 220: 245–250). These strains contain the binary vectors conferring resistance to kanamycin (nptII), basta (bar) and hygromycin (hpt), respectively, all under the control of the nopalin-synthase (NOS) promoter and terminator. Bacteria are cultured with the proper antibiotics in liquid LB medium for 24 hours at 28° C. at 200 rpm.

Cocultivation

For studying the sensitivity of grape embryogenic calli to different Agrobacterium strains, bacterial cultures with different optical densities (0.1–0.7 at 630 nm) are prepared from an overnight culture of Agrobacterium strains. Bacteria are centrifuged 5 minutes, 5000 rpm and resuspended in antibiotic free McCown's Woody Plant Medium (WPM) (Lloyd and McCown, 1981, Int Plant Prop Soc Proc 30: 421–427). Three grams fresh weight of embryogenic calli (7 days after transfer to NOA containing medium) are resuspended in 10 ml of overnight cultured bacterial suspensions for 5 minutes, dry blotted and transferred to Petri dishes containing regeneration medium [basal WPM medium supplemented with thidiazuron (TDZ) (0.5 mg/L), Zeatin riboside (ZR) (0.5 mg/L), and sucrose (3%)]. The regeneration medium is solidified with gelrite (0.25% w/v) and the calli, after initial drainage of excess bacteria, are cocultivated in the dark at 25° C. for different times (5 minutes up to 7 days). For stable transformation experiments, inoculum (OD 0.6 at 630 nm) is prepared from an overnight culture of LBA 4404 or GVE 3101. Bacteria are centrifuged 5 minutes, 5000 rpm and resuspended in antibiotic-free WPM medium.

Embryogenic calli (3 g fresh weight) are resuspended in 10 ml of bacteria for 5 minutes, dry blotted and transferred to Petri dishes containing solidified (0.25% w/v) gelrite regeneration medium supplemented with different antioxidants. The calli are cocultivated for 48 hours in the dark at 25° C.

Selective Culture

Following 48 hours of cocultivation, the embryogenic callus is maintained in the dark for 7 days on antioxidant containing regeneration medium. Subsequently, the calli are collected on a sterile metal screen and transferred to fresh WPM regeneration medium at 25° C. under 40 $\mu E/m^2/s$ (white fluorescent tubes). All regeneration media are supplemented with 400 mg/L claforan, 1.5 g/L malt extract and different selectable markers: kanamycin (50–500 mg/L), hygromycin (15 mg/L) and Basta (1–10 mg/L). Periodic increases in hygromycin concentration are used. The putative transformed calli are cultured on regeneration medium supplemented with 15 mg/L hygromycin. Every two weeks the regenerating calli are transferred to fresh medium supplemented with 20 and 25 mg/L hygromycin respectively. Control, untransformed grape calli are also cultured on selective media and are periodically exposed to increasing hygromycin concentrations. Green adventitious embryos, which developed on calli cultured for 8–10 weeks on selective regeneration medium, are transferred to germination medium. Embryo germination, rooting and subsequent plantlet development are induced on WPM as described (Perl et al, 1995, Plant Sci 104: 193–200), supplemented with 25 mg/L hygromycin or 10 mg/L basta. Conversion of vitrified abnormal plantlets into normal-looking grape plantlets are obtained using solidified WPM medium supplemented with 0.1 mg/L NAA as described (Perl et al, 1995, Plant Sci 104: 193–200).

Transgenic Potatoes

General teachings on potato transformation may be found in our copending patent applications PCT/EP96/03053, PCT/EP96/03052 and PCT/EP94/01082 (the contents of each of which are incorporated herein by reference).

For the present studies, the following protocol is adopted.

Plasmid Construction

The disarmed *Agrobacterium tumefaciens* strain LBA 4404, containing the helper vir plasmid pRAL4404 (Hoekema et al, 1983 Nature 303 pp 179–180), is cultured on YMB agar ($K_2HPO_4.3H_2O$ 660 mg $1^{-1}$, $MgSO_4$ 200 mg $1^{-1}$, NaCl 100 mg $1^{-1}$, mannitol 10 g $1^{-1}$, yeast extract 400 mg $1^{-1}$, 0.8% w/v agar, pH 7.0) containing 100 mg $1^{-1}$ rifampicin and 500 mg $1^{-1}$ streptomycin sulphate. Transformation with pVICTOR IV GNG E35S nagB IV2' or pVICTOR IV GNG rbc nagB IV2' or pVICTOR IV GNG E35S nagB' (which correspond to each of pVICTOR IV GNG E35S nagB IV2 or pVICTOR IV GNG rbc nagB IV2 or pVICTOR IV GNG E35S nagB but wherein each of those plasmids also contains any one of the nucleotide sequences shown as SEQ ID No.s. 7–12 operatively linked to a functional promoter) is accomplished using the freeze-thaw method of Holters et al (1978 Mol Gen Genet 163 181–187) and transformants are selected on YMB agar containing 100 mg $1^{-1}$ rifampicin and 500 mg $1^{-1}$ streptomycin, and 50 mg $1^{-1}$ gentamycin sulphate.

Transformation of Plants

Shoot cultures of *Solanum tuberosum* cv Saturna are maintained on LS agar containing Murashige Skoog basal salts (Sigma M6899) (Murashige and Skoog, 1965, Physiol Plant 15 473–497) with 2 $\mu M$ silver thiosulphate, and nutrients and vitamins as described by Linsmaier and Skoog (1965 Physiol Plant 18 100–127). Cultures are maintained at 25° C. with a 16 h daily photoperiod. After approximately 40 days, subculturing is performed during which leaves are removed, and the shoots cut into mononodal segments of approximately 8 mm length.

Shoot cultures of approximately 40 days maturity (5–6 cm height) are cut into 8 mm internodal segments which are placed into liquid LS-medium containing *Agrobacterium tumefaciens* transformed with pVICTOR IV GNG E35S nagB IV2' or pVICTOR IV GNG rbc nagB IV2' or pVICTOR IV GNG E35S nagB' ($A_{660}$=0.5, pathlength 1 cm). Following incubation at room temperature for 30 minutes, the segments are dried by blotting on to sterile filter paper and transferred to LS agar (0.8% w/v containing 2 mg $l^{-1}$ 2,4-D and 500 µg $l^{-1}$ trans-zeatin. The explants are covered with filter paper, moistened with LS medium, and covered with a cloth for three days at 25° C. Following this treatment, the segments are washed with liquid LS medium containing 800 mg $l^{-1}$ carbenicillin, and transferred on to LS agar (0.8% w/v) containing 1 mg $l^{-1}$ trans-zeatin, 100 µg $l^{-1}$ gibberellic acid (GA3), with sucrose (eg 7.5 g $l^{-1}$) and glucosamine (eg 2.5 g $l^{-1}$) as the selection agent.

The segments are sub-cultured to fresh substrate each 3–4 weeks. In 3 to 4 weeks, shoots develop from the segments and the formation of new shoots continues for 3–4 months.

Rooting of Regenerated Shoots

The regenerated shoots are transferred to rooting substrate composed of LS-substrate, agar (8 g/l) and carbenicillin (800 mg/l).

The transgenic plants may be verified by performing a GUS assay on the co-introduced β-glucuronidase gene according to Hodal, L. et al. (Pl. Sci. (1992), 87: 115–122).

Alternatively, the transgenic genotype of the regenerated shoot may be verified by performing NPTII assays (Radke, S. E. et al, Theor. Appl. Genet. (1988), 75: 685–694) or by performing PCR analysis according to Wang et al (1993, NAR 21 pp 4153–4154).

Transfer to Soil

The newly rooted plants (height approx. 2–3 cms) are transplanted from rooting substrate to soil and placed in a growth chamber (21° C., 16 hour light 200–400 uE/m²/sec). When the plants are well established they are transferred to the greenhouse, where they are grown until tubers had developed and the upper part of the plants are senescing.

Harvesting

The potatoes are harvested after about 3 months.

Transgenic Maize Plants

Introduction

Since the first publication of production of transgenic plants in 1983 (Leemans, 1993 Biotechnology 11 s22), there have been numerous publications of production of transgenic plants including especially dicotyledon crop plants.

Until very recently there are very few reports on successful production of transgenic monocotyledononary crop plants. This relatively slow development within monocots are due to two causes. Firstly, until the early 1980s, efficient regeneration of plants from cultured cells and tissues of monocots had proven very difficult. This problem is ultimately solved by the culture of explants from immature and embryogenic tissue, which retain their morphogenic potential on nutrient media containing plant growth regulators. Secondly, the monocots are not a natural host for *Agrobacterium tumefaciens*, meaning that the successful developed techniques within the dicots using their natural vector *Agrobacterium tumefaciens* is unsuccessful for many years in the monocots.

Nevertheless, it is now possible to successfully transformation and produce fertile transgenic plants of maize using methods such as: (1) Silicon Carbide Whiskers; (2) Particle Bombardment; (3) DNA Uptake by PEG treated protoplast; or (4) DNA Uptake in Electroporation of Tissue. Each of these methods—which are reviewed by Thompson (1995 Euphtytica 85 pp 75–80)—may be used to prepare inter alia transgenic maize according to the present invention.

In particular, the particle Gun method has been successfully used for the transformation of monocots. However, EP-A-0604662 reports on a different method of transforming monocotyledons. The method comprises transforming cultured tissues of a monocotyledon under or after dedifferentiation with Agrobacterium containing a super binary vector as a selectable marker a hygromycin-resistant gene is used. Production of transgenic calli and plant is demonstrated using the hygromycin selection. This method may be used to prepare inter alia transgenic maize according to the present invention.

Subsequent to the method of EP-A-0604662, EP-A-0672752 reports on non-dedifferentiated immature embryos. In this regard, both hygromycin-resistance and PPT-resistance genes are used as the selectable marker, with PPT giving rise to 10% or more independent transformed plants. This method may be used to prepare inter alia transgenic maize according to the present invention.

To date, it would appear that transgenic maize plants can be successfully produced from easily-culturable varieties—such as the inbred line A188. In this regard, see the teachings of Ishida et al (1996 Nature Biotechnology 14 pp 745–750). The method disclosed by these workers may be used to prepare inter alia transgenic maize according to the present invention.

Vasil (1996 Nature Biotechnology 14 pp 702–703) presents a further review article on transformation of maize. Even though it is possible to prepare transformed maize by use of, for example, particle Gun mediated transformation, for the present studies the following protocol is adopted.

Plasmid Construction

The disarmed *Agrobacterium tumefaciens* strain LBA 4404, containing the helper vir plasmid pRAL4404 (Hoekema et al, 1983 Nature 303 pp 179–180), is cultured on YMB agar ($K_2HPO_4.3H_2O$ 660 mg $l^{-1}$, $MgSO_4$ 200 mg $l^{-1}$, NaCl 100 mg $l^{-1}$, mannitol 10 g $l^{-1}$, yeast extract 400 mg $l^{-1}$, 0.8% w/v agar, pH 7.0) containing 100 mg $l^{-1}$ rifampicin and 500 mg $l^{-1}$ streptomycin sulphate. Transformation with pVICTOR IV GNG E35S nagB IV2' or pVICTOR IV GNG rbc nagB IV2' or pVICTOR IV GNG E35S nagB' is accomplished using the freeze-thaw method of Holters et al (1978 Mol Gen Genet 163 181–187) and transformants are selected on YMB agar containing 100 mg $l^{-1}$ rifampicin and 500 mg $l^{-1}$ streptomycin, and 50 mg $l^{-1}$ gentamycin sulphate.

Isolation and Cocultivation of Explants

Immature embryos of, for example, maize line A188 of the size between 1.5 to 2.5 mm are isolated and cocultivated with *Agrobacterium tumefaciens* strain LBA 4404 in N6-AS for 2–3 days at 25° C. under illumination. Thereafter, the embryos are washed with sterilized water containing 250 mg/l of cefotaxime and transferred to an LS medium and 250 mg/l cefotaxime and glucosamine in concentrations of up to 100 mg/l (the medium is hereafter called LSS1).

Conditions for the Selection of Transgenic Plants

The explants are cultured for three weeks on LSS1 medium and then transferred to an LS medium containing glucosamine and cefotaxime. After three weeks on this medium, green shoots are isolated.

Rooting of Transformed Shoots

Transformed shoots are transferred to an MS medium containing 2 mg/l for rooting. After four weeks on this medium, plantlets are transferred to pots with sterile soil for acclimatisation.

Transgenic Guar Plants

Transformation of guar cotyledonary explants is performed according to Joersbo and Okkels (PCT/DK95/00221) using *Agrobacterium tumefaciens* LBA4404 harbouring a suitable plasmid.

Other plants may be transformed in accordance with the present invention, such as other fruits, other vegetables, and other plants such as coffee plants, tea plants etc.

Other modifications of the present invention will be apparent to those skilled in the art.

What is claimed is:

1. A method for increasing anhydrofructose levels in a plant or part thereof, the method comprising introducing a nucleic acid encoding α-1,4-glucan lyase in the plant or part thereof, wherein the α-1,4-glucan lyase is expressed and acts on a glucan substrate present in the plant or part thereof to yield increased levels of anhydrofructose in the plant or part thereof, wherein the α-1,4-glucan lyase comprises an amino acid sequence having at least 75% sequence identity to SEQ ID NO: 1, SEQ ID NO: 2, SEQ ID NO: 3, SEQ ID NO. 4, SEQ ID NO: 5 or SEQ ID NO: 6.

2. The method of claim 1, further comprising preparing from said plant or part thereof a foodstuff.

3. The method of claim 1, wherein the α-1,4-glucan lyase comprises SEQ ID NO: 1, SEQ ID NO: 2, SEQ ID NO: 3, SEQ ID NO: 4, SEQ ID NO: 5 or SEQ ID NO: 6.

4. The method of claim 1, wherein the nucleic acid encoding α-1,4-glucan lyase comprises SEQ ID NO: 7, SEQ ID NO: 8, SEQ ID NO: 9, SEQ ID NO: 10, SEQ ID NO: 11 or SEQ ID NO: 12.

5. The method of claim 1, wherein the nucleic acid comprised SEQ ID NO: 7.

6. The method of claim 1, wherein the α-1,4-glucan lyase has at least 75% identity to the sequence shown as SEQ ID NO: 1.

7. The method of claim 1, wherein the α-1,4-glucan lyase has at least 85% identity to the sequence shown as SEQ ID NO: 1.

8. The method of claim 1, wherein the α-1,4-glucan lyase has at least 90% identity to the sequence shown as SEQ ID NO: 1.

9. The method of claim 1, wherein the plant or part thereof is a fruit or a vegetable.

10. The method of claim 1, wherein the plant is grape.

11. The method of claim 1, wherein the plant is potato.

12. The method of claim 2, wherein the foodstuff is a beverage.

13. The method of claim 12, wherein the beverage is an alcoholic beverage.

14. The method of claim 12, wherein the beverage is wine.

15. A method of preparing a foodstuff comprising anhydrofructose, said method comprising the steps of:
 a) introducing a nucleic acid encoding α-1,4-glucan lyase in a plant or part thereof, wherein the α-1,4-glucan lyase is expressed and acts on a glucan substrate present in the plant or part thereof to yield anhydrofructose in the plant or part thereof, and wherein the α-1,4-glucan lyase comprises an amino acid sequence having at least 75% sequence identity to SEQ ID NO: 1, SEQ ID NO: 2, SEQ ID NO: 3, SEQ ID NO: 4, SEQ ID NO: 5 or SEQ ID NO: 6; and
 b) preparing a foodstuff comprising the plant or part thereof, whereby the foodstuff comprises the anhydrofructose yielded in step a).

16. The method of claim 15, wherein the α-1,4-glucan lyase comprises SEQ ID NO: 1, SEQ ID NO: 2, SEQ ID NO: 3, SEQ ID NO: 4, SEQ ID NO: 5 or SEQ ID NO: 6.

17. The method of claim 15, wherein the nucleic acid encoding α-1,4-glucan lyase comprises SEQ ID NO: 7, SEQ ID NO: 8, SEQ ID NO: 9, SEQ ID NO: 10, SEQ ID NO: 11 or SEQ ID NO: 12.

18. The method of claim 15, wherein the nucleic acid comprises SEQ ID NO: 7.

19. The method of claim 15, wherein the α-1,4-glucan lyase has at least 75% identity to the sequence shown as SEQ ID NO: 1.

20. The method of claim 15, wherein the α-1,4-glucan lyase has at least 85% identity to the sequence shown as SEQ ID NO: 1.

21. The method of claim 15, wherein the α-1,4-glucan lyase has at least 90% identity to the sequence shown as SEQ ID NO: 1.

22. The method of claim 15, wherein the plant or part thereof is a fruit or a vegetable.

23. The method of claim 15, wherein the plant is grape.

24. The method of claim 15, wherein the plant is potato.

25. The method of claim 15, wherein the foodstuff is a beverage.

26. The method of claim 25, wherein the beverage is an alcoholic beverage.

27. The method of claim 25, wherein the beverage is wine.

* * * * *

SEQUENCE LISTING

<160> NUMBER OF SEQ ID NOS: 12

<210> SEQ ID NO 1
<211> LENGTH: 1088
<212> TYPE: PRT
<213> ORGANISM: Unknown
<220> FEATURE:
<223> OTHER INFORMATION: fungus sp. or fungus infected gracilariopsis sp.

<400> SEQUENCE: 1

```
Met Phe Ser Thr Leu Ala Phe Val Ala Pro Ser Ala Leu Gly Ala Ser
1               5                   10                  15

Thr Phe Val Gly Ala Glu Val Arg Ser Asn Val Arg Ile His Ser Ala
            20                  25                  30

Phe Pro Ala Val His Thr Ala Thr Arg Lys Thr Asn Arg Leu Asn Val
        35                  40                  45

Ser Met Thr Ala Leu Ser Asp Lys Gln Thr Ala Thr Ala Gly Ser Thr
    50                  55                  60

Asp Asn Pro Asp Gly Ile Asp Tyr Lys Thr Tyr Asp Tyr Val Gly Val
65                  70                  75                  80

Trp Gly Phe Ser Pro Leu Ser Asn Thr Asn Trp Phe Ala Ala Gly Ser
                85                  90                  95

Ser Thr Pro Gly Gly Ile Thr Asp Trp Thr Ala Thr Met Asn Val Asn
            100                 105                 110

Phe Asp Arg Ile Asp Asn Pro Ser Ile Thr Val Gln His Pro Val Gln
        115                 120                 125

Val Gln Val Thr Ser Tyr Asn Asn Asn Ser Tyr Arg Val Arg Phe Asn
    130                 135                 140

Pro Asp Gly Pro Ile Arg Asp Val Thr Arg Gly Pro Ile Leu Lys Gln
145                 150                 155                 160

Gln Leu Asp Trp Ile Arg Thr Gln Glu Leu Ser Glu Gly Cys Asp Pro
                165                 170                 175

Gly Met Thr Phe Thr Ser Glu Gly Phe Leu Thr Phe Glu Thr Lys Asp
            180                 185                 190

Leu Ser Val Ile Ile Tyr Gly Asn Phe Lys Thr Arg Val Thr Arg Lys
        195                 200                 205

Ser Asp Gly Lys Val Ile Met Glu Asn Asp Glu Val Gly Thr Ala Ser
    210                 215                 220

Ser Gly Asn Lys Cys Arg Gly Leu Met Phe Val Asp Arg Leu Tyr Gly
225                 230                 235                 240

Asn Ala Ile Ala Ser Val Asn Lys Asn Phe Arg Asn Asp Ala Val Lys
                245                 250                 255

Gln Glu Gly Phe Tyr Gly Ala Gly Glu Val Asn Cys Lys Tyr Gln Asp
            260                 265                 270

Thr Tyr Ile Leu Glu Arg Thr Gly Ile Ala Met Thr Asn Tyr Asn Tyr
        275                 280                 285

Asp Asn Leu Asn Tyr Asn Gln Trp Asp Leu Arg Pro Pro His His Asp
    290                 295                 300
```

-continued

```
Gly Ala Leu Asn Pro Asp Tyr Tyr Ile Pro Met Tyr Ala Ala Pro
305                 310                 315                 320

Trp Leu Ile Val Asn Gly Cys Ala Gly Thr Ser Glu Gln Tyr Ser Tyr
                325                 330                 335

Gly Trp Phe Met Asp Asn Val Ser Gln Ser Tyr Met Asn Thr Gly Asp
            340                 345                 350

Thr Thr Trp Asn Ser Gly Gln Glu Asp Leu Ala Tyr Met Gly Ala Gln
        355                 360                 365

Tyr Gly Pro Phe Asp Gln His Phe Val Tyr Gly Ala Gly Gly Gly Met
    370                 375                 380

Glu Cys Val Val Thr Ala Phe Ser Leu Leu Gln Gly Lys Glu Phe Glu
385                 390                 395                 400

Asn Gln Val Leu Asn Lys Arg Ser Val Met Pro Pro Lys Tyr Val Phe
                405                 410                 415

Gly Phe Phe Gln Gly Val Phe Gly Thr Ser Ser Leu Leu Arg Ala His
            420                 425                 430

Met Pro Ala Gly Glu Asn Asn Ile Ser Val Glu Glu Ile Val Glu Gly
        435                 440                 445

Tyr Gln Asn Asn Asn Phe Pro Phe Glu Gly Leu Ala Val Asp Val Asp
    450                 455                 460

Met Gln Asp Asn Leu Arg Val Phe Thr Thr Lys Gly Glu Phe Trp Thr
465                 470                 475                 480

Ala Asn Arg Val Gly Thr Gly Asp Pro Asn Asn Arg Ser Val Phe
                485                 490                 495

Glu Trp Ala His Asp Lys Gly Leu Val Cys Gln Thr Asn Ile Thr Cys
            500                 505                 510

Phe Leu Arg Asn Asp Asn Glu Gly Gln Asp Tyr Glu Val Asn Gln Thr
        515                 520                 525

Leu Arg Glu Arg Gln Leu Tyr Thr Lys Asn Asp Ser Leu Thr Gly Thr
    530                 535                 540

Asp Phe Gly Met Thr Asp Asp Gly Pro Ser Asp Ala Tyr Ile Gly His
545                 550                 555                 560

Leu Asp Tyr Gly Gly Val Glu Cys Asp Ala Leu Phe Pro Asp Trp
                565                 570                 575

Gly Arg Pro Asp Val Ala Glu Trp Trp Gly Asn Asn Tyr Lys Lys Leu
            580                 585                 590

Phe Ser Ile Gly Leu Asp Phe Val Trp Gln Asp Met Thr Val Pro Ala
        595                 600                 605

Met Met Pro His Lys Ile Gly Asp Asp Ile Asn Val Lys Pro Asp Gly
    610                 615                 620

Asn Trp Pro Asn Ala Asp Asp Pro Ser Asn Gly Gln Tyr Asn Trp Lys
625                 630                 635                 640

Thr Tyr His Pro Gln Val Leu Val Thr Asp Met Arg Tyr Glu Asn His
                645                 650                 655

Gly Arg Glu Pro Met Val Thr Gln Arg Asn Ile His Ala Tyr Thr Leu
            660                 665                 670

Cys Glu Ser Thr Arg Lys Glu Gly Ile Val Glu Asn Ala Asp Thr Leu
        675                 680                 685

Thr Lys Phe Arg Arg Ser Tyr Ile Ile Ser Arg Gly Gly Tyr Ile Gly
    690                 695                 700

Asn Gln His Phe Gly Gly Met Trp Val Gly Asp Asn Ser Thr Thr Ser
705                 710                 715                 720

Asn Tyr Ile Gln Met Met Ile Ala Asn Asn Ile Asn Met Asn Met Ser
```

-continued

```
                725                 730                 735
Cys Leu Pro Leu Val Gly Ser Asp Ile Gly Gly Phe Thr Ser Tyr Asp
            740                 745                 750
Asn Glu Asn Gln Arg Thr Pro Cys Thr Gly Asp Leu Met Val Arg Tyr
        755                 760                 765
Val Gln Ala Gly Cys Leu Leu Pro Trp Phe Arg Asn His Tyr Asp Arg
    770                 775                 780
Trp Ile Glu Ser Lys Asp His Gly Lys Asp Tyr Gln Glu Leu Tyr Met
785                 790                 795                 800
Tyr Pro Asn Glu Met Asp Thr Leu Arg Lys Phe Val Glu Phe Arg Tyr
            805                 810                 815
Arg Trp Gln Glu Val Leu Tyr Thr Ala Met Tyr Gln Asn Ala Ala Phe
        820                 825                 830
Gly Lys Pro Ile Ile Lys Ala Ala Ser Met Tyr Asn Asn Asp Ser Asn
            835                 840                 845
Val Arg Arg Ala Gln Asn Asp His Phe Leu Leu Gly Gly His Asp Gly
    850                 855                 860
Tyr Arg Ile Leu Cys Ala Pro Val Val Trp Glu Asn Ser Thr Glu Arg
865                 870                 875                 880
Glu Leu Tyr Leu Pro Val Leu Thr Gln Trp Tyr Lys Phe Gly Pro Asp
                885                 890                 895
Phe Asp Thr Lys Pro Leu Glu Gly Ala Met Asn Gly Gly Asp Arg Ile
            900                 905                 910
Tyr Asn Tyr Pro Val Pro Gln Ser Glu Ser Pro Ile Phe Val Arg Glu
        915                 920                 925
Gly Ala Ile Leu Pro Thr Arg Tyr Thr Leu Asn Gly Glu Asn Lys Ser
    930                 935                 940
Leu Asn Thr Tyr Thr Asp Glu Asp Pro Leu Val Phe Glu Val Phe Pro
945                 950                 955                 960
Leu Gly Asn Asn Arg Ala Asp Gly Met Cys Tyr Leu Asp Asp Gly Gly
                965                 970                 975
Val Thr Thr Asn Ala Glu Asp Asn Gly Lys Phe Ser Val Val Lys Val
            980                 985                 990
Ala Ala Glu Gln Asp Gly Gly Thr Glu Thr Ile Thr Phe Thr Asn Asp
        995                 1000                1005
Cys Tyr Glu Tyr Val Phe Gly Gly Pro Phe Tyr Val Arg Val Arg
    1010                1015                1020
Gly Ala Gln Ser Pro Ser Asn Ile His Val Ser Ser Gly Ala Gly
    1025                1030                1035
Ser Gln Asp Met Lys Val Ser Ser Ala Thr Ser Arg Ala Ala Leu
    1040                1045                1050
Phe Asn Asp Gly Glu Asn Gly Asp Phe Trp Val Asp Gln Glu Thr
    1055                1060                1065
Asp Ser Leu Trp Leu Lys Leu Pro Asn Val Val Leu Pro Asp Ala
    1070                1075                1080
Val Ile Thr Ile Thr
    1085
```

<210> SEQ ID NO 2
<211> LENGTH: 1091
<212> TYPE: PRT
<213> ORGANISM: Unknown
<220> FEATURE:
<223> OTHER INFORMATION: fungus sp. or fungus infected gracilariopsis sp.

<400> SEQUENCE: 2

```
Met Tyr Pro Thr Leu Thr Phe Val Ala Pro Ser Ala Leu Gly Ala Arg
 1               5                  10                  15
Thr Phe Thr Cys Val Gly Ile Phe Arg Ser His Ile Leu Ile His Ser
            20                  25                  30
Val Val Pro Ala Val Arg Leu Ala Val Arg Lys Ser Asn Arg Leu Asn
        35                  40                  45
Val Ser Met Ser Ala Leu Phe Asp Lys Pro Thr Ala Val Thr Gly Gly
    50                  55                  60
Lys Asp Asn Pro Asp Asn Ile Asn Tyr Thr Thr Tyr Asp Tyr Val Pro
 65                  70                  75                  80
Val Trp Arg Phe Asp Pro Leu Ser Asn Thr Asn Trp Phe Ala Ala Gly
                85                  90                  95
Ser Ser Thr Pro Gly Asp Ile Asp Asp Trp Thr Ala Thr Met Asn Val
            100                 105                 110
Asn Phe Asp Arg Ile Asp Asn Pro Ser Phe Thr Leu Glu Lys Pro Val
        115                 120                 125
Gln Val Gln Val Thr Ser Tyr Lys Asn Asn Cys Phe Arg Val Arg Phe
    130                 135                 140
Asn Pro Asp Gly Pro Ile Arg Asp Val Asp Arg Gly Pro Ile Leu Gln
145                 150                 155                 160
Gln Gln Leu Asn Trp Ile Arg Lys Gln Glu Gln Ser Lys Gly Phe Asp
                165                 170                 175
Pro Lys Met Gly Phe Thr Lys Glu Gly Phe Leu Lys Phe Glu Thr Lys
            180                 185                 190
Asp Leu Asn Val Ile Ile Tyr Gly Asn Phe Lys Thr Arg Val Thr Arg
        195                 200                 205
Lys Arg Asp Gly Lys Gly Ile Met Glu Asn Asn Glu Val Pro Ala Gly
    210                 215                 220
Ser Leu Gly Asn Lys Cys Arg Gly Leu Met Phe Val Asp Arg Leu Tyr
225                 230                 235                 240
Gly Thr Ala Ile Ala Ser Val Asn Glu Asn Tyr Arg Asn Asp Pro Asp
                245                 250                 255
Arg Lys Glu Gly Phe Tyr Gly Ala Gly Glu Val Asn Cys Glu Phe Trp
            260                 265                 270
Asp Ser Glu Gln Asn Arg Asn Lys Tyr Ile Leu Glu Arg Thr Gly Ile
        275                 280                 285
Ala Met Thr Asn Tyr Asn Tyr Asp Asn Tyr Asn Tyr Asn Gln Ser Asp
    290                 295                 300
Leu Ile Ala Pro Gly Tyr Pro Ser Asp Pro Asn Phe Tyr Ile Pro Met
305                 310                 315                 320
Tyr Phe Ala Ala Pro Trp Val Val Lys Gly Cys Ser Gly Asn Ser
                325                 330                 335
Asp Glu Gln Tyr Ser Tyr Gly Trp Phe Met Asp Asn Val Ser Gln Thr
            340                 345                 350
Tyr Met Asn Thr Gly Gly Thr Ser Trp Asn Cys Gly Glu Glu Asn Leu
        355                 360                 365
Ala Tyr Met Gly Ala Gln Cys Gly Pro Phe Asp Gln His Phe Val Tyr
    370                 375                 380
Gly Asp Gly Asp Gly Leu Glu Asp Val Val Gln Ala Phe Ser Leu Leu
385                 390                 395                 400
Gln Gly Lys Glu Phe Glu Asn Gln Val Leu Asn Lys Arg Ala Val Met
```

-continued

```
                405                 410                 415
Pro Pro Lys Tyr Val Phe Gly Tyr Phe Gln Gly Val Phe Gly Ile Ala
            420                 425                 430
Ser Leu Leu Arg Glu Gln Arg Pro Glu Gly Asn Asn Ile Ser Val
            435                 440                 445
Gln Glu Ile Val Glu Gly Tyr Gln Ser Asn Asn Phe Pro Leu Glu Gly
            450                 455                 460
Leu Ala Val Asp Val Asp Met Gln Gln Asp Leu Arg Val Phe Thr Thr
465                 470                 475                 480
Lys Ile Glu Phe Trp Thr Ala Asn Lys Val Gly Thr Gly Gly Asp Ser
                485                 490                 495
Asn Asn Lys Ser Val Phe Glu Trp Ala His Asp Lys Gly Leu Val Cys
            500                 505                 510
Gln Thr Asn Val Thr Cys Phe Leu Arg Asn Asp Asn Gly Gly Ala Asp
            515                 520                 525
Tyr Glu Val Asn Gln Thr Leu Arg Glu Lys Gly Leu Tyr Thr Lys Asn
            530                 535                 540
Asp Ser Leu Thr Asn Thr Asn Phe Gly Thr Thr Asn Asp Gly Pro Ser
545                 550                 555                 560
Asp Ala Tyr Ile Gly His Leu Asp Tyr Gly Gly Gly Asn Cys Asp
                565                 570                 575
Ala Leu Phe Pro Asp Trp Gly Arg Pro Gly Val Ala Glu Trp Trp Gly
            580                 585                 590
Asp Asn Tyr Ser Lys Leu Phe Lys Ile Gly Leu Asp Phe Val Trp Gln
            595                 600                 605
Asp Met Thr Val Pro Ala Met Met Pro His Lys Val Gly Asp Ala Val
            610                 615                 620
Asp Thr Arg Ser Pro Tyr Gly Trp Pro Asn Glu Asn Asp Pro Ser Asn
625                 630                 635                 640
Gly Arg Tyr Asn Trp Lys Ser Tyr His Pro Gln Val Leu Val Thr Asp
                645                 650                 655
Met Arg Tyr Glu Asn His Gly Arg Glu Pro Met Phe Thr Gln Arg Asn
                660                 665                 670
Met His Ala Tyr Thr Leu Cys Glu Ser Thr Arg Lys Glu Gly Ile Val
            675                 680                 685
Ala Asn Ala Asp Thr Leu Thr Lys Phe Arg Arg Ser Tyr Ile Ile Ser
            690                 695                 700
Arg Gly Gly Tyr Ile Gly Asn Gln His Phe Gly Gly Met Trp Val Gly
705                 710                 715                 720
Asp Asn Ser Ser Ser Gln Arg Tyr Leu Gln Met Met Ile Ala Asn Ile
                725                 730                 735
Val Asn Met Asn Met Ser Cys Leu Pro Leu Val Gly Ser Asp Ile Gly
            740                 745                 750
Gly Phe Thr Ser Tyr Asp Gly Arg Asn Val Cys Pro Gly Asp Leu Met
            755                 760                 765
Val Arg Phe Val Gln Ala Gly Cys Leu Leu Pro Trp Phe Arg Asn His
            770                 775                 780
Tyr Gly Arg Leu Val Glu Gly Lys Gln Glu Gly Lys Tyr Tyr Gln Glu
785                 790                 795                 800
Leu Tyr Met Tyr Lys Asp Glu Met Ala Thr Leu Arg Lys Phe Ile Glu
                805                 810                 815
Phe Arg Tyr Arg Trp Gln Glu Val Leu Tyr Thr Ala Met Tyr Gln Asn
                820                 825                 830
```

-continued

```
Ala Ala Phe Gly Lys Pro Ile Ile Lys Ala Ser Met Tyr Asp Asn
            835                 840                 845

Asp Arg Asn Val Arg Gly Ala Gln Asp Asp His Phe Leu Leu Gly Gly
    850                 855                 860

His Asp Gly Tyr Arg Ile Leu Cys Ala Pro Val Val Trp Glu Asn Thr
865                 870                 875                 880

Thr Ser Arg Asp Leu Tyr Leu Pro Val Leu Thr Lys Trp Tyr Lys Phe
                885                 890                 895

Gly Pro Asp Tyr Asp Thr Lys Arg Leu Asp Ser Ala Leu Asp Gly Gly
                900                 905                 910

Gln Met Ile Lys Asn Tyr Ser Val Pro Gln Ser Asp Ser Pro Ile Phe
                915                 920                 925

Val Arg Glu Gly Ala Ile Leu Pro Thr Arg Tyr Thr Leu Asp Gly Ser
                930                 935                 940

Asn Lys Ser Met Asn Thr Tyr Thr Asp Lys Asp Pro Leu Val Phe Glu
945                 950                 955                 960

Val Phe Pro Leu Gly Asn Asn Arg Ala Asp Gly Met Cys Tyr Leu Asp
                965                 970                 975

Asp Gly Gly Ile Thr Thr Asp Ala Glu Asp His Gly Lys Phe Ser Val
                980                 985                 990

Ile Asn Val Glu Ala Leu Arg Lys Gly Val Thr Thr Thr Ile Lys Phe
                995                1000                1005

Ala Tyr Asp Thr Tyr Gln Tyr Val Phe Asp Gly Pro Phe Tyr Val
        1010                1015                1020

Arg Ile Arg Asn Leu Thr Thr Ala Ser Lys Ile Asn Val Ser Ser
        1025                1030                1035

Gly Ala Gly Glu Glu Asp Met Thr Pro Thr Ser Ala Asn Ser Arg
        1040                1045                1050

Ala Ala Leu Phe Ser Asp Gly Gly Val Gly Glu Tyr Trp Ala Asp
        1055                1060                1065

Asn Asp Thr Ser Ser Leu Trp Met Lys Leu Pro Asn Leu Val Leu
        1070                1075                1080

Gln Asp Ala Val Ile Thr Ile Thr
        1085                1090
```

```
<210> SEQ ID NO 3
<211> LENGTH: 1066
<212> TYPE: PRT
<213> ORGANISM: Unknown
<220> FEATURE:
<223> OTHER INFORMATION: fungus sp. or fungus infected gracilariopsis
      sp.

<400> SEQUENCE: 3

Met Ala Gly Phe Ser Asp Pro Leu Asn Phe Cys Lys Ala Glu Asp Tyr
1               5                   10                  15

Tyr Ser Val Ala Leu Asp Trp Lys Gly Pro Gln Lys Ile Ile Gly Val
            20                  25                  30

Asp Thr Thr Pro Pro Lys Ser Thr Lys Phe Pro Lys Asn Trp His Gly
        35                  40                  45

Val Asn Leu Arg Phe Asp Asp Gly Thr Leu Gly Val Val Gln Phe Ile
    50                  55                  60

Arg Pro Cys Val Trp Arg Val Arg Tyr Asp Pro Gly Phe Lys Thr Ser
65                  70                  75                  80

Asp Glu Tyr Gly Asp Glu Asn Thr Arg Thr Ile Val Gln Asp Tyr Met
```

```
                    85                  90                  95
Ser Thr Leu Ser Asn Lys Leu Asp Thr Tyr Arg Gly Leu Thr Trp Glu
                100                 105                 110

Thr Lys Cys Glu Asp Ser Gly Asp Phe Phe Thr Phe Ser Ser Lys Val
        115                 120                 125

Thr Ala Val Glu Lys Ser Glu Arg Thr Arg Asn Lys Val Gly Asp Gly
    130                 135                 140

Leu Arg Ile His Leu Trp Lys Ser Pro Phe Arg Ile Gln Val Val Arg
145                 150                 155                 160

Thr Leu Thr Pro Leu Lys Asp Pro Tyr Pro Ile Pro Asn Val Ala Ala
                165                 170                 175

Ala Glu Ala Arg Val Ser Asp Lys Val Val Trp Gln Thr Ser Pro Lys
            180                 185                 190

Thr Phe Arg Lys Asn Leu His Pro Gln His Lys Met Leu Lys Asp Thr
        195                 200                 205

Val Leu Asp Ile Val Lys Pro Gly His Gly Glu Tyr Val Gly Trp Gly
    210                 215                 220

Glu Met Gly Gly Ile Gln Phe Met Lys Glu Pro Thr Phe Met Asn Tyr
225                 230                 235                 240

Phe Asn Phe Asp Asn Met Gln Tyr Gln Gln Val Tyr Ala Gln Gly Ala
                245                 250                 255

Leu Asp Ser Arg Glu Pro Leu Tyr His Ser Asp Pro Phe Tyr Leu Asp
            260                 265                 270

Val Asn Ser Asn Pro Glu His Lys Asn Ile Thr Ala Thr Phe Ile Asp
        275                 280                 285

Asn Tyr Ser Gln Ile Ala Ile Asp Phe Gly Lys Thr Asn Ser Gly Tyr
    290                 295                 300

Ile Lys Leu Gly Thr Arg Tyr Gly Gly Ile Asp Cys Tyr Gly Ile Ser
305                 310                 315                 320

Ala Asp Thr Val Pro Glu Ile Val Arg Leu Tyr Thr Gly Leu Val Gly
                325                 330                 335

Arg Ser Lys Leu Lys Pro Arg Tyr Ile Leu Gly Ala His Gln Ala Cys
            340                 345                 350

Tyr Gly Tyr Gln Gln Glu Ser Asp Leu Tyr Ser Val Val Gln Gln Tyr
        355                 360                 365

Arg Asp Cys Lys Phe Pro Leu Asp Gly Ile His Val Asp Val Asp Val
    370                 375                 380

Gln Asp Gly Phe Arg Thr Phe Thr Thr Asn Pro His Thr Phe Pro Asn
385                 390                 395                 400

Pro Lys Glu Met Phe Thr Asn Leu Arg Asn Asn Gly Ile Lys Cys Ser
                405                 410                 415

Thr Asn Ile Thr Pro Val Ile Ser Ile Asn Asn Arg Glu Gly Gly Tyr
            420                 425                 430

Ser Thr Leu Leu Glu Gly Val Asp Lys Lys Tyr Phe Ile Met Asp Asp
        435                 440                 445

Arg Tyr Thr Glu Gly Thr Ser Gly Asn Ala Lys Asp Val Arg Tyr Met
    450                 455                 460

Tyr Tyr Gly Gly Gly Asn Lys Val Glu Val Asp Pro Asn Asp Val Asn
465                 470                 475                 480

Gly Arg Pro Asp Phe Lys Asp Asn Tyr Asp Phe Pro Ala Asn Phe Asn
                485                 490                 495

Ser Lys Gln Tyr Pro Tyr His Gly Gly Val Ser Tyr Gly Tyr Gly Asn
            500                 505                 510
```

-continued

```
Gly Ser Ala Gly Phe Tyr Pro Asp Leu Asn Arg Lys Glu Val Arg Ile
            515                 520                 525
Trp Trp Gly Met Gln Tyr Lys Tyr Leu Phe Asp Met Gly Leu Glu Phe
        530                 535                 540
Val Trp Gln Asp Met Thr Thr Pro Ala Ile His Thr Ser Tyr Gly Asp
545                 550                 555                 560
Met Lys Gly Leu Pro Thr Arg Leu Leu Val Thr Ser Asp Ser Val Thr
                565                 570                 575
Asn Ala Ser Glu Lys Lys Leu Ala Ile Glu Thr Trp Ala Leu Tyr Ser
            580                 585                 590
Tyr Asn Leu His Lys Ala Thr Trp His Gly Leu Ser Arg Leu Glu Ser
        595                 600                 605
Arg Lys Asn Lys Arg Asn Phe Ile Leu Gly Arg Gly Ser Tyr Ala Gly
    610                 615                 620
Ala Tyr Arg Phe Ala Gly Leu Trp Thr Gly Asp Asn Ala Ser Asn Trp
625                 630                 635                 640
Glu Phe Trp Lys Ile Ser Val Ser Gln Val Leu Ser Leu Gly Leu Asn
                645                 650                 655
Gly Val Cys Ile Ala Gly Ser Asp Thr Gly Gly Phe Glu Pro Tyr Arg
            660                 665                 670
Asp Ala Asn Gly Val Glu Glu Lys Tyr Cys Ser Pro Glu Leu Leu Ile
        675                 680                 685
Arg Trp Tyr Thr Gly Ser Phe Leu Leu Pro Trp Leu Arg Asn His Tyr
    690                 695                 700
Val Lys Lys Asp Arg Lys Trp Phe Gln Glu Pro Tyr Ser Tyr Pro Lys
705                 710                 715                 720
His Leu Glu Thr His Pro Glu Leu Ala Asp Gln Ala Trp Leu Tyr Lys
                725                 730                 735
Ser Val Leu Glu Ile Cys Arg Tyr Tyr Val Glu Leu Arg Tyr Ser Leu
            740                 745                 750
Ile Gln Leu Leu Tyr Asp Cys Met Phe Gln Asn Val Val Asp Gly Met
        755                 760                 765
Pro Ile Thr Arg Ser Met Leu Leu Thr Asp Thr Glu Asp Thr Thr Phe
    770                 775                 780
Phe Asn Glu Ser Gln Lys Phe Leu Asp Asn Gln Tyr Met Ala Gly Asp
785                 790                 795                 800
Asp Ile Leu Val Ala Pro Ile Leu His Ser Arg Lys Glu Ile Pro Gly
                805                 810                 815
Glu Asn Arg Asp Val Tyr Leu Pro Leu Tyr His Thr Trp Tyr Pro Ser
            820                 825                 830
Asn Leu Arg Pro Trp Asp Asp Gln Gly Val Ala Leu Gly Asn Pro Val
        835                 840                 845
Glu Gly Gly Ser Val Ile Asn Tyr Thr Ala Arg Ile Val Ala Pro Glu
    850                 855                 860
Asp Tyr Asn Leu Phe His Ser Val Val Pro Val Tyr Val Arg Glu Gly
865                 870                 875                 880
Ala Ile Ile Pro Gln Ile Glu Val Arg Gln Trp Thr Gly Gln Gly Gly
                885                 890                 895
Ala Asn Arg Ile Lys Phe Asn Ile Tyr Pro Gly Lys Asp Lys Glu Tyr
            900                 905                 910
Cys Thr Tyr Leu Asp Asp Gly Val Ser Arg Asp Ser Ala Pro Glu Asp
        915                 920                 925
```

-continued

```
Leu Pro Gln Tyr Lys Glu Thr His Glu Gln Ser Lys Val Glu Gly Ala
    930                 935                 940

Glu Ile Ala Lys Gln Ile Gly Lys Lys Thr Gly Tyr Asn Ile Ser Gly
945                 950                 955                 960

Thr Asp Pro Glu Ala Lys Gly Tyr His Arg Lys Val Ala Val Thr Gln
                965                 970                 975

Thr Ser Lys Asp Lys Thr Arg Thr Val Thr Ile Glu Pro Lys His Asn
            980                 985                 990

Gly Tyr Asp Pro Ser Lys Glu Val Gly Asp Tyr Tyr Thr Ile Ile Leu
        995                 1000                1005

Trp Tyr Ala Pro Gly Phe Asp Gly Ser Ile Val Asp Val Ser Lys
    1010                1015                1020

Thr Thr Val Asn Val Glu Gly Gly Val Glu His Gln Val Tyr Lys
    1025                1030                1035

Asn Ser Asp Leu His Thr Val Val Ile Asp Val Lys Glu Val Ile
    1040                1045                1050

Gly Thr Thr Lys Ser Val Lys Ile Thr Cys Thr Ala Ala
    1055                1060                1065

<210> SEQ ID NO 4
<211> LENGTH: 1070
<212> TYPE: PRT
<213> ORGANISM: Unknown
<220> FEATURE:
<223> OTHER INFORMATION: fungus sp. or fungus infected gracilariopsis
      sp.

<400> SEQUENCE: 4

Met Ala Gly Leu Ser Asp Pro Leu Asn Phe Cys Lys Ala Glu Asp Tyr
1               5                   10                  15

Tyr Ala Ala Lys Gly Trp Ser Gly Pro Gln Lys Ile Ile Arg Tyr
            20                  25                  30

Asp Gln Thr Pro Pro Gln Gly Thr Lys Asp Pro Lys Ser Trp His Ala
            35                  40                  45

Val Asn Leu Pro Phe Asp Asp Gly Thr Met Cys Val Val Gln Phe Val
        50                  55                  60

Arg Pro Cys Val Trp Arg Val Arg Tyr Asp Pro Ser Val Lys Thr Ser
65                  70                  75                  80

Asp Glu Tyr Gly Asp Glu Asn Thr Arg Thr Ile Val Gln Asp Tyr Met
                85                  90                  95

Thr Thr Leu Val Gly Asn Leu Asp Ile Phe Arg Gly Leu Thr Trp Val
            100                 105                 110

Ser Thr Leu Glu Asp Ser Gly Glu Tyr Tyr Thr Phe Lys Ser Glu Val
            115                 120                 125

Thr Ala Val Asp Glu Thr Glu Arg Thr Arg Asn Lys Val Gly Asp Gly
        130                 135                 140

Leu Lys Ile Tyr Leu Trp Lys Asn Pro Phe Arg Ile Gln Val Val Arg
145                 150                 155                 160

Leu Leu Thr Pro Leu Val Asp Pro Phe Pro Ile Pro Asn Val Ala Asn
                165                 170                 175

Ala Thr Ala Arg Val Ala Asp Lys Val Val Trp Gln Thr Ser Pro Lys
            180                 185                 190

Thr Phe Arg Lys Asn Leu His Pro Gln His Lys Met Leu Lys Asp Thr
        195                 200                 205

Val Leu Asp Ile Ile Lys Pro Gly His Gly Glu Tyr Val Gly Trp Gly
    210                 215                 220
```

-continued

```
Glu Met Gly Gly Ile Glu Phe Met Lys Glu Pro Thr Phe Met Asn Tyr
225                 230                 235                 240

Phe Asn Phe Asp Asn Met Gln Tyr Gln Gln Val Tyr Ala Gln Gly Ala
            245                 250                 255

Leu Asp Ser Arg Glu Pro Leu Tyr His Ser Asp Pro Phe Tyr Leu Asp
            260                 265                 270

Val Asn Ser Asn Pro Glu His Lys Asn Ile Thr Ala Thr Phe Ile Asp
            275                 280                 285

Asn Tyr Ser Gln Ile Ala Ile Asp Phe Gly Lys Thr Asn Ser Gly Tyr
        290                 295                 300

Ile Lys Leu Gly Thr Arg Tyr Gly Gly Ile Asp Cys Tyr Gly Ile Ser
305                 310                 315                 320

Ala Asp Thr Val Pro Glu Ile Val Arg Leu Tyr Thr Gly Leu Val Gly
                325                 330                 335

Arg Ser Lys Leu Lys Pro Arg Tyr Ile Leu Gly Ala His Gln Ala Cys
            340                 345                 350

Tyr Gly Tyr Gln Gln Glu Ser Asp Leu His Ala Val Gln Gln Tyr
        355                 360                 365

Arg Asp Thr Lys Phe Pro Leu Asp Gly Leu His Val Asp Val Asp Phe
    370                 375                 380

Gln Asp Asn Phe Arg Thr Phe Thr Thr Asn Pro Ile Thr Phe Pro Asn
385                 390                 395                 400

Pro Lys Glu Met Phe Thr Asn Leu Arg Asn Asn Gly Ile Lys Cys Ser
                405                 410                 415

Thr Asn Ile Thr Pro Val Ile Ser Ile Arg Asp Arg Pro Asn Gly Tyr
            420                 425                 430

Ser Thr Leu Asn Glu Gly Tyr Asp Lys Lys Tyr Phe Ile Met Asp Asp
        435                 440                 445

Arg Tyr Thr Glu Gly Thr Ser Gly Asp Pro Gln Asn Val Arg Tyr Ser
450                 455                 460

Phe Tyr Gly Gly Gly Asn Pro Val Glu Val Asn Pro Asn Asp Val Trp
465                 470                 475                 480

Ala Arg Pro Asp Phe Gly Asp Asn Tyr Asp Phe Pro Thr Asn Phe Asn
            485                 490                 495

Cys Lys Asp Tyr Pro Tyr His Gly Gly Val Ser Tyr Gly Tyr Gly Asn
            500                 505                 510

Gly Thr Pro Gly Tyr Tyr Pro Asp Leu Asn Arg Glu Glu Val Arg Ile
        515                 520                 525

Trp Trp Gly Leu Gln Tyr Glu Tyr Leu Phe Asn Met Gly Leu Glu Phe
        530                 535                 540

Val Trp Gln Asp Met Thr Thr Pro Ala Ile His Ser Ser Tyr Gly Asp
545                 550                 555                 560

Met Lys Gly Leu Pro Thr Arg Leu Leu Val Thr Ala Asp Ser Val Thr
                565                 570                 575

Asn Ala Ser Glu Lys Lys Leu Ala Ile Glu Ser Trp Ala Leu Tyr Ser
            580                 585                 590

Tyr Asn Leu His Lys Ala Thr Phe His Gly Leu Gly Arg Leu Glu Ser
            595                 600                 605

Arg Lys Asn Lys Arg Asn Phe Ile Leu Gly Arg Gly Ser Tyr Ala Gly
        610                 615                 620

Ala Tyr Arg Phe Ala Gly Leu Trp Thr Gly Asp Asn Ala Ser Thr Trp
625                 630                 635                 640
```

-continued

```
Glu Phe Trp Lys Ile Ser Val Ser Gln Val Leu Ser Leu Gly Leu Asn
                645                 650                 655
Gly Val Cys Ile Ala Gly Ser Asp Thr Gly Gly Phe Glu Pro Ala Arg
            660                 665                 670
Thr Glu Ile Gly Glu Lys Tyr Cys Ser Pro Glu Leu Leu Ile Arg
        675                 680                 685
Trp Tyr Thr Gly Ser Phe Leu Leu Pro Trp Leu Arg Asn His Tyr Val
    690                 695                 700
Lys Lys Asp Arg Lys Trp Phe Gln Glu Pro Tyr Ala Tyr Pro Lys His
705                 710                 715                 720
Leu Glu Thr His Pro Glu Leu Ala Asp Gln Ala Trp Leu Tyr Lys Ser
                725                 730                 735
Val Leu Glu Ile Cys Arg Tyr Trp Val Glu Leu Arg Tyr Ser Leu Ile
            740                 745                 750
Gln Leu Leu Tyr Asp Cys Met Phe Gln Asn Val Val Asp Gly Met Pro
        755                 760                 765
Leu Ala Arg Ser Met Leu Leu Thr Asp Thr Glu Asp Thr Thr Phe Phe
    770                 775                 780
Asn Glu Ser Gln Lys Phe Leu Asp Asn Gln Tyr Met Ala Gly Asp Asp
785                 790                 795                 800
Ile Leu Val Ala Pro Ile Leu His Ser Arg Asn Glu Val Pro Gly Glu
                805                 810                 815
Asn Arg Asp Val Tyr Leu Pro Leu Phe His Thr Trp Tyr Pro Ser Asn
            820                 825                 830
Leu Arg Pro Trp Asp Asp Gln Gly Val Ala Leu Gly Asn Pro Val Glu
        835                 840                 845
Gly Gly Ser Val Ile Asn Tyr Thr Ala Arg Ile Val Ala Pro Glu Asp
    850                 855                 860
Tyr Asn Leu Phe His Asn Val Val Pro Val Tyr Ile Arg Glu Gly Ala
865                 870                 875                 880
Ile Ile Pro Gln Ile Gln Val Arg Gln Trp Ile Gly Glu Gly Gly Pro
                885                 890                 895
Asn Pro Ile Lys Phe Asn Ile Tyr Pro Gly Lys Asp Lys Glu Tyr Val
            900                 905                 910
Thr Tyr Leu Asp Asp Gly Val Ser Arg Asp Ser Ala Pro Asp Asp Leu
        915                 920                 925
Pro Gln Tyr Arg Glu Ala Tyr Glu Gln Ala Lys Val Glu Gly Lys Asp
    930                 935                 940
Val Gln Lys Gln Leu Ala Val Ile Gln Gly Asn Lys Thr Asn Asp Phe
945                 950                 955                 960
Ser Ala Ser Gly Ile Asp Lys Glu Ala Lys Gly Tyr His Arg Lys Val
                965                 970                 975
Ser Ile Lys Gln Glu Ser Lys Asp Lys Thr Arg Thr Val Thr Ile Glu
            980                 985                 990
Pro Lys His Asn Gly Tyr Asp Pro  Ser Lys Glu Val Gly  Asn Tyr Tyr
        995                 1000                1005
Thr Ile  Ile Leu Trp Tyr Ala  Pro Gly Phe Asp Gly  Ser Ile Val
    1010                1015                1020
Asp Val  Ser Gln Ala Thr Val  Asn Ile Glu Gly Gly  Val Glu Cys
    1025                1030                1035
Glu Ile  Phe Lys Asn Thr Gly  Leu His Thr Val Val  Val Asn Val
    1040                1045                1050
Lys Glu  Val Ile Gly Thr Thr  Lys Ser Val Lys Ile  Thr Cys Thr
```

```
            1055                1060                1065

Thr Ala
    1070

<210> SEQ ID NO 5
<211> LENGTH: 1092
<212> TYPE: PRT
<213> ORGANISM: Unknown
<220> FEATURE:
<223> OTHER INFORMATION: fungus sp. or fungus infected gracilariopsis
      sp.

<400> SEQUENCE: 5

Met Phe Pro Thr Leu Thr Phe Ile Ala Pro Ser Ala Leu Ala Ala Ser
1               5                  10                  15

Thr Phe Val Gly Ala Asp Ile Arg Gly Ile Arg Ile Gln Ser Ala
            20                  25                  30

Leu Pro Ala Val Arg Asn Ala Val Arg Arg Ser Lys His Tyr Asn Val
            35                  40                  45

Ser Met Thr Ala Leu Ser Asp Lys Gln Thr Ala Ile Ser Ile Gly Pro
50                  55                  60

Asp Asn Pro Asp Gly Ile Asn Tyr Gln Asn Tyr Asp Tyr Ile Pro Val
65                  70                  75                  80

Ala Gly Phe Thr Pro Leu Ser Asn Thr Asn Trp Tyr Ala Ala Gly Ser
                85                  90                  95

Ser Thr Pro Gly Gly Ile Thr Asp Trp Thr Ala Thr Met Asn Val Lys
            100                 105                 110

Phe Asp Arg Ile Asp Asn Pro Ser Tyr Ser Asn Asn His Pro Val Gln
            115                 120                 125

Ile Gln Val Thr Ser Tyr Asn Asn Ser Phe Arg Ile Arg Phe Asn
            130                 135                 140

Pro Asp Gly Pro Ile Arg Asp Val Ser Arg Gly Pro Ile Leu Lys Gln
145                 150                 155                 160

Gln Leu Thr Trp Ile Arg Asn Gln Glu Leu Ala Gln Gly Cys Asn Pro
                165                 170                 175

Asn Met Ser Phe Ser Pro Glu Gly Phe Leu Ser Phe Glu Thr Lys Asp
            180                 185                 190

Leu Asn Val Ile Ile Tyr Gly Asn Cys Lys Met Arg Val Thr Lys Lys
            195                 200                 205

Asp Gly Tyr Leu Val Met Glu Asn Asp Glu Cys Asn Ser Gln Ser Asp
    210                 215                 220

Gly Asn Lys Cys Arg Gly Leu Met Tyr Val Asp Arg Leu Tyr Gly Asn
225                 230                 235                 240

Ala Ile Ala Ser Val Gln Thr Asn Phe His Lys Asp Thr Ser Arg Asn
                245                 250                 255

Glu Lys Phe Tyr Gly Ala Gly Glu Val Asn Cys Arg Tyr Glu Glu Gln
            260                 265                 270

Gly Lys Ala Pro Thr Tyr Val Leu Glu Arg Ser Gly Leu Ala Met Thr
            275                 280                 285

Asn Tyr Asn Tyr Asp Asn Leu Asn Tyr Asn Gln Pro Asp Val Val Pro
    290                 295                 300

Pro Gly Tyr Pro Asp His Pro Asn Tyr Ile Pro Met Tyr Tyr Ala
305                 310                 315                 320

Ala Pro Trp Leu Val Val Gln Gly Cys Ala Gly Thr Ser Lys Gln Tyr
                325                 330                 335
```

-continued

```
Ser Tyr Gly Trp Phe Met Asp Asn Val Ser Gln Ser Tyr Met Asn Thr
                340                 345                 350
Gly Asp Thr Ala Trp Asn Cys Gly Gln Glu Asn Leu Ala Tyr Met Gly
            355                 360                 365
Ala Gln Tyr Gly Pro Phe Asp Gln His Phe Val Tyr Gly Asp Gly Asp
        370                 375                 380
Gly Leu Glu Asp Val Val Lys Ala Phe Ser Phe Leu Gln Gly Lys Glu
385                 390                 395                 400
Phe Glu Asp Lys Lys Leu Asn Lys Arg Ser Val Met Pro Pro Lys Tyr
                405                 410                 415
Val Phe Gly Phe Phe Gln Gly Val Phe Gly Ala Leu Ser Leu Leu Lys
            420                 425                 430
Gln Asn Leu Pro Ala Gly Glu Asn Asn Ile Ser Val Gln Glu Ile Val
        435                 440                 445
Glu Gly Tyr Gln Asp Asn Asp Tyr Pro Phe Glu Gly Leu Ala Val Asp
450                 455                 460
Val Asp Met Gln Asp Asp Leu Arg Val Phe Thr Thr Lys Pro Glu Tyr
465                 470                 475                 480
Trp Ser Ala Asn Met Val Gly Glu Gly Gly Asp Pro Asn Asn Arg Ser
                485                 490                 495
Val Phe Glu Trp Ala His Asp Arg Gly Leu Val Cys Gln Thr Asn Val
            500                 505                 510
Thr Cys Phe Leu Arg Asn Asp Asn Ser Gly Lys Pro Tyr Glu Val Asn
        515                 520                 525
Gln Thr Leu Arg Glu Lys Gln Leu Tyr Thr Lys Asn Asp Ser Leu Asn
        530                 535                 540
Asn Thr Asp Phe Gly Thr Thr Ser Asp Gly Pro Gly Asp Ala Tyr Ile
545                 550                 555                 560
Gly His Leu Asp Tyr Gly Gly Val Glu Cys Asp Ala Ile Phe Pro
                565                 570                 575
Asp Trp Gly Arg Pro Asp Val Ala Gln Trp Trp Gly Glu Asn Tyr Lys
            580                 585                 590
Lys Leu Phe Ser Ile Gly Leu Asp Phe Val Trp Gln Asp Met Thr Val
        595                 600                 605
Pro Ala Met Met Pro His Arg Leu Gly Asp Ala Val Asn Lys Asn Ser
        610                 615                 620
Gly Ser Ser Ala Pro Gly Trp Pro Asn Glu Asn Asp Pro Ser Asn Gly
625                 630                 635                 640
Arg Tyr Asn Trp Lys Ser Tyr His Pro Gln Val Leu Val Thr Asp Met
                645                 650                 655
Arg Tyr Gly Ala Glu Tyr Gly Arg Glu Pro Met Val Ser Gln Arg Asn
            660                 665                 670
Ile His Ala Tyr Thr Leu Cys Glu Ser Thr Arg Arg Glu Gly Ile Val
        675                 680                 685
Gly Asn Ala Asp Ser Leu Thr Lys Phe Arg Arg Ser Tyr Ile Ile Ser
        690                 695                 700
Arg Gly Gly Tyr Ile Gly Asn Gln His Phe Gly Met Trp Val Gly
705                 710                 715                 720
Asp Asn Ser Ala Thr Glu Ser Tyr Leu Gln Met Met Leu Ala Asn Ile
                725                 730                 735
Ile Asn Met Asn Met Ser Cys Leu Pro Leu Val Gly Ser Asp Ile Gly
            740                 745                 750
Gly Phe Thr Gln Tyr Asn Asp Ala Gly Asp Pro Thr Pro Glu Asp Leu
```

755                 760                 765
Met Val Arg Phe Val Gln Ala Gly Cys Leu Leu Pro Trp Phe Arg Asn
770                 775                 780

His Tyr Asp Arg Trp Ile Glu Ser Lys Lys His Gly Lys Lys Tyr Gln
785                 790                 795                 800

Glu Leu Tyr Met Tyr Pro Gly Gln Lys Asp Thr Leu Lys Lys Phe Val
                805                 810                 815

Glu Phe Arg Tyr Arg Trp Gln Glu Val Leu Tyr Thr Ala Met Tyr Gln
                820                 825                 830

Asn Ala Thr Thr Gly Glu Pro Ile Ile Lys Ala Ala Pro Met Tyr Asn
                835                 840                 845

Asn Asp Val Asn Val Tyr Lys Ser Gln Asn Asp His Phe Leu Leu Gly
850                 855                 860

Gly His Asp Gly Tyr Arg Ile Leu Cys Ala Pro Val Val Arg Glu Asn
865                 870                 875                 880

Ala Thr Ser Arg Glu Val Tyr Leu Pro Val Tyr Ser Lys Trp Phe Lys
                885                 890                 895

Phe Gly Pro Asp Phe Asp Thr Lys Pro Leu Glu Asn Glu Ile Gln Gly
                900                 905                 910

Gly Gln Thr Leu Tyr Asn Tyr Ala Ala Pro Leu Asn Asp Ser Pro Ile
                915                 920                 925

Phe Val Arg Glu Gly Thr Ile Leu Pro Thr Arg Tyr Thr Leu Asp Gly
930                 935                 940

Val Asn Lys Ser Ile Asn Thr Tyr Thr Asp Asn Asp Pro Leu Val Phe
945                 950                 955                 960

Glu Leu Phe Pro Leu Glu Asn Asn Gln Ala His Gly Leu Phe Tyr His
                965                 970                 975

Asp Asp Gly Gly Val Thr Thr Asn Ala Glu Asp Phe Gly Lys Tyr Ser
                980                 985                 990

Val Ile Ser Val Lys Ala Ala Gln Glu Gly Ser Gln Met Ser Val Lys
                995                 1000                1005

Phe Asp Asn Glu Val Tyr Glu His Gln Trp Gly Ala Ser Phe Tyr
   1010                1015                1020

Val Arg Val Arg Asn Met Gly Ala Pro Ser Asn Ile Asn Val Ser
   1025                1030                1035

Ser Gln Ile Gly Gln Gln Asp Met Gln Ser Ser Val Ser Ser
   1040                1045                1050

Arg Ala Gln Met Phe Thr Ser Ala Asn Asp Gly Glu Tyr Trp Val
   1055                1060                1065

Asp Gln Ser Thr Asn Ser Leu Trp Leu Lys Leu Pro Gly Ala Val
   1070                1075                1080

Ile Gln Asp Ala Ala Ile Thr Val Arg
   1085                1090

<210> SEQ ID NO 6
<211> LENGTH: 570
<212> TYPE: PRT
<213> ORGANISM: Unknown
<220> FEATURE:
<223> OTHER INFORMATION: fungus sp. or fungus infected gracilariopsis
      sp.

<400> SEQUENCE: 6

Met Thr Asn Tyr Asn Tyr Asp Asn Leu Asn Tyr Asn Gln Pro Asp Leu
1               5                   10                  15

```
Ile Pro Pro Gly His Asp Ser Asp Pro Asp Tyr Tyr Ile Pro Met Tyr
            20                  25                  30

Phe Ala Ala Pro Trp Val Ile Ala His Gly Tyr Arg Gly Thr Ser Asp
            35                  40                  45

Gln Tyr Ser Tyr Gly Trp Phe Leu Asp Asn Val Ser Gln Ser Tyr Thr
 50                  55                  60

Asn Thr Gly Asp Asp Ala Trp Ala Gly Gln Lys Asp Leu Ala Tyr Met
 65                  70                  75                  80

Gly Ala Gln Cys Gly Pro Phe Asp Gln His Phe Val Tyr Glu Ala Gly
                 85                  90                  95

Asp Gly Leu Glu Asp Val Val Thr Ala Phe Ser Tyr Leu Gln Gly Lys
            100                 105                 110

Glu Tyr Glu Asn Gln Gly Leu Asn Ile Arg Ser Ala Met Pro Pro Lys
            115                 120                 125

Tyr Val Phe Gly Phe Phe Gln Gly Val Phe Gly Ala Thr Ser Leu Leu
            130                 135                 140

Arg Asp Asn Leu Pro Ala Gly Glu Asn Asn Val Ser Leu Glu Glu Ile
145                 150                 155                 160

Val Glu Gly Tyr Gln Asn Gln Asn Val Pro Phe Glu Gly Leu Ala Val
                165                 170                 175

Asp Val Asp Met Gln Asp Asp Leu Arg Val Phe Thr Thr Arg Pro Ala
            180                 185                 190

Phe Trp Thr Ala Asn Lys Val Gly Glu Gly Gly Asp Pro Asn Asn Lys
            195                 200                 205

Ser Val Phe Glu Trp Ala His Asp Arg Gly Leu Val Cys Gln Thr Asn
210                 215                 220

Val Thr Cys Phe Leu Lys Asn Glu Lys Asn Pro Tyr Glu Val Asn Gln
225                 230                 235                 240

Ser Leu Arg Glu Lys Gln Leu Tyr Thr Lys Ser Asp Ser Leu Asp Asn
            245                 250                 255

Ile Asp Phe Gly Thr Thr Pro Asp Gly Pro Ser Asp Ala Tyr Ile Gly
            260                 265                 270

His Leu Asp Tyr Gly Gly Val Glu Cys Asp Ala Leu Phe Pro Asp
            275                 280                 285

Trp Gly Arg Pro Asp Val Ala Gln Trp Trp Gly Asp Asn Tyr Lys Lys
            290                 295                 300

Leu Phe Ser Ile Gly Leu Asp Phe Val Trp Gln Asp Met Thr Val Pro
305                 310                 315                 320

Ala Met Met Pro His Arg Leu Gly Asp Pro Val Gly Thr Asn Ser Gly
                325                 330                 335

Glu Thr Ala Pro Gly Trp Pro Asn Asp Lys Asp Pro Ser Asn Gly Arg
            340                 345                 350

Tyr Asn Trp Lys Ser Tyr His Pro Gln Val Leu Val Thr Asp Met Arg
            355                 360                 365

Tyr Asp Asp Tyr Gly Arg Asp Pro Ile Val Thr Gln Arg Asn Leu His
            370                 375                 380

Ala Tyr Thr Leu Cys Glu Ser Thr Arg Arg Glu Gly Ile Val Gly Asn
385                 390                 395                 400

Ala Asp Ser Leu Thr Lys Phe Arg Arg Ser Tyr Ile Ile Ser Arg Gly
                405                 410                 415

Gly Tyr Ile Gly Asn Gln His Phe Gly Gly Met Trp Val Gly Asp Asn
            420                 425                 430

Ser Ser Thr Glu Asp Tyr Leu Ala Met Met Val Ile Asn Val Ile Asn
```

```
                 435              440              445
Met Asn Met Ser Gly Val Pro Leu Val Gly Ser Asp Ile Gly Gly Phe
        450              455              460

Thr Glu His Asp Lys Arg Asn Pro Cys Thr Pro Asp Leu Met Met Arg
465              470              475              480

Phe Val Gln Ala Gly Cys Leu Leu Pro Trp Phe Arg Asn His Tyr Asp
                485              490              495

Arg Trp Ile Glu Ser Lys Lys His Gly Lys Asn Tyr Gln Glu Leu Tyr
            500              505              510

Met Tyr Arg Asp His Leu Asp Ala Leu Arg Ser Phe Val Glu Leu Arg
        515              520              525

Tyr Arg Trp Gln Glu Val Leu Tyr Thr Ala Met Tyr Gln Asn Ala Leu
    530              535              540

Asn Gly Lys Pro Ile Ile Lys Thr Val Ser Met Tyr Asn Asn Asp Met
545              550              555              560

Asn Val Lys Asp Ala Gln Asn Asp His Phe
                565              570

<210> SEQ ID NO 7
<211> LENGTH: 3267
<212> TYPE: DNA
<213> ORGANISM: Unknown
<220> FEATURE:
<223> OTHER INFORMATION: fungus sp. or fungus infected gracilariopsis
      sp.

<400> SEQUENCE: 7
atgttttcaa cccttgcgtt tgtcgcacct agtgcgctgg gagccagtac cttcgtaggg       60
gcggaggtca ggtcaaatgt tcgtatccat tccgcttttc cagctgtgca cacagctact      120
cgcaaaacca atcgcctcaa tgtatccatg accgcattgt ccgacaaaca aacggctact      180
gcgggtagta cagacaatcc ggacggtatc gactacaaga cctacgatta cgtcggagta      240
tggggtttca gcccctctc caacacgaac tggtttgctg ccggctcttc taccccgggt       300
ggcatcactg attggacggc tacaatgaat gtcaacttcg accgtatcga caatccgtcc      360
atcactgtcc agcatcccgt tcaggttcag gtcacgtcat acaacaacaa cagctacagg      420
gttcgcttca accctgatgg ccctattcgt gatgtgactc gtgggcctat cctcaagcag      480
caactagatt ggattcgaac gcaggagctg tcagagggat gtgatcccgg aatgactttc      540
acatcagaag gtttcttgac ttttgagacc aaggatctaa gcgtcatcat ctacggaaat      600
ttcaagacca gagttacgag aaagtctgac ggcaaggtca tcatggaaaa tgatgaagtt      660
ggaactgcat cgtccgggaa caagtgccgg ggattgatgt tcgttgatag attatacggt      720
aacgctatcg cttccgtcaa caagaacttc cgcaacgacg cggtcaagca ggagggattc      780
tatggtgcag gtgaagtcaa ctgtaagtac caggacacct acatcttaga acgcactgga      840
atcgccatga caaattacaa ctacgataac ttgaactata ccagtgggac ccttagacct      900
ccgcatcatg atggtgccct caacccagac tattatattc caatgtacta cgcagcacct      960
tggttgatcg ttaatggatg cgccggtact tcggagcagt actcgtatgg atggttcatg     1020
gacaatgtct ctcaatctta catgaatact ggagatacta cctggaattc tggacaagag     1080
gacctggcat acatgggcgc gcagtatgga ccatttgacc aacattttgt ttacggtgct     1140
gggggtggga tggaatgtgt ggtcacagcg ttctctcttc tacaaggcaa ggagttcgag     1200
aaccaagttc tcaacaaacg ttcagtaatg cctccgaaat acgtctttgg tttcttccag     1260
```

```
ggtgttttcg ggacttcttc cttgttgaga gcgcatatgc cagcaggtga gaacaacatc    1320
tcagtcgaag aaattgtaga aggttatcaa acaacaatt tccctttcga ggggctcgct     1380
gtggacgtgg atatgcaaga caacttgcgg gtgttcacca cgaagggcga attttggacc    1440
gcaaacaggg tgggtactgg cggggatcca acaaccgat cggttttga atgggcacat      1500 gacaaaggcc ttgtttgtca gacaaatata acttgcttcc tgaggaatga taacgagggg   1560
caagactacg aggtcaatca gacgttaagg gagaggcagt tgtacacgaa gaacgactcc   1620
ctgacgggta cggattttgg aatgaccgac gacggcccca gcgatgcgta catcggtcat   1680
ctggactatg ggggtggagt agaatgtgat gcacttttcc cagactgggg acggcctgac   1740
gtggccgaat ggtggggaaa taactataag aaactgttca gcattggtct cgacttcgtc   1800
tggcaagaca tgactgttcc agcaatgatg ccgcacaaaa ttggcgatga catcaatgtg   1860
aaaccggatg ggaattggcc gaatgcggac gatccgtcca atggacaata caactggaag   1920
acgtaccatc cccaagtgct tgtaactgat atgcgttatg agaatcatgg tcgggaaccg   1980
atggtcactc aacgcaacat tcatgcgtat acactgtgcg agtctactag gaaggaaggg   2040
atcgtggaaa acgcagacac tctaacgaag ttccgccgta gctacattat cagtcgtggt   2100
ggttacattg gtaaccagca tttcgggggt atgtgggtgg gagacaactc tactacatca   2160
aactacatcc aaatgatgat tgccaacaat attaacatga atatgtcttg cttgcctctc   2220
gtcggctccg acattggagg attcacctca tacgacaatg agaatcagcg aacgccgtgt   2280
accggggact tgatggtgag gtatgtgcag gcgggctgcc tgttgccgtg gttcaggaac   2340
cactatgata ggtggatcga gtccaaggac cacggaaagg actaccagga gctgtacatg   2400
tatccgaatg aaatggatac gttgaggaag ttcgttgaat tccgttatcg ctggcaggaa   2460
gtgttgtaca cggccatgta ccagaatgcg gctttcgaa agccgattat caaggctgct   2520
tcgatgtaca ataacgactc aaacgttcgc agggcgcaga acgatcattt ccttcttggt   2580
ggacatgatg gatatcgcat tctgtgcgcg cctgttgtgt gggagaattc gaccgaacgc   2640
gaattgtact tgcccgtgct gacccaatgg tacaaattcg gtcccgactt tgacaccaag   2700
cctctggaag gagcgatgaa cggaggggac cgaatttaca actaccctgt accgcaaagt   2760
gaatcaccaa tcttcgtgag agaaggtgcg attctcccta cccgctacac gttgaacgt   2820 gaaaacaaat cattgaacac gtacacggac gaagatccgt tggtgtttga agtattcccc   2880
ctcggaaaca accgtgccga cggtatgtgt tatcttgatg atggcggtgt gaccaccaat   2940
gctgaagaca atgcaagtt ctctgtcgtc aaggtggcag cggagcagga tggtggtacg    3000
gagacgataa cgtttacgaa tgattgctat gagtacgttt tcggtggacc gttctacgtt   3060
cgagtgcgcg cgctcagtc gccgtcgaac atccacgtgt cttctggagc gggttctcag    3120
gacatgaagg tgagctctgc cacttccagg gctgcgctgt tcaatgacgg ggagaacggt   3180
gatttctggg ttgaccagga gacagattct ctgtggctga agttgcccaa cgttgttctc   3240
ccggacgctg tgatcacaat tacctaa                                       3267
```

<210> SEQ ID NO 8
<211> LENGTH: 3276
<212> TYPE: DNA
<213> ORGANISM: Unknown
<220> FEATURE:
<223> OTHER INFORMATION: fungus sp. or fungus infected gracilariopsis sp.

<400> SEQUENCE: 8

```
atgtatccaa ccctcacctt cgtggcgcct agtgcgctag gggccagaac tttcacgtgt      60
gtgggcattt ttaggtcaca cattcttatt cattcggttg ttccagcggt gcgtctagct     120
gtgcgcaaaa gcaaccgcct caatgtatcc atgtccgctt tgttcgacaa accgactgct     180
gttactggag ggaaggacaa cccggacaat atcaattaca ccacttatga ctacgtccct     240
gtgtggcgct tcgaccccct cagcaatacg aactggtttg ctgccggatc ttccactccc     300
ggcgatattg acgactggac ggcgacaatg aatgtgaact tcgaccgtat cgacaatcca     360
tccttcactc tcgagaaacc ggttcaggtt caggtcacgt catacaagaa caattgtttc     420
agggttcgct tcaaccctga tggtcctatt cgcgatgtgg atcgtgggcc tatcctccag     480
cagcaactaa attggatccg gaagcaggag cagtcgaagg ggtttgatcc taagatgggc     540
ttcacaaaag aaggtttctt gaaatttgag accaaggatc tgaacgttat catatatggc     600
aattttaaga ctagagttac gaggaagagg gatggaaaag gatcatggaa gaataatgaa     660
gtgccggcag gatcgttagg gaacaagtgc cggggattga tgtttgtcga caggttgtac     720
ggcactgcca tcgcttccgt taatgaaaat taccgcaacg atcccgacag gaaagagggg     780
ttctatggtg caggagaagt aaactgcgag ttttgggact ccgaacaaaa caggaacaag     840
tacatcttag aacgaactgg aatcgccatg acaaattaca attatgacaa ctataactac     900
aaccagtcag atcttattgc tccaggatat ccttccgacc cgaacttcta cattcccatg     960
tattttgcag caccttgggt agttgttaag ggatgcagtg gcaacagcga tgaacagtac    1020
tcgtacggat ggtttatgga taatgtctcc caaacttaca tgaatactgg tggtacttcc    1080
tggaactgtg agaggagaaa cttggcatac atgggagcac agtgcggtcc atttgaccaa    1140
cattttgtgt atggtgatgg agatggtctt gaggatgttg tccaagcgtt ctctcttctg    1200
caaggcaaag agtttgagaa ccaagttctg aacaaacgtg ccgtaatgcc tccgaaatat    1260
gtgtttggtt actttcaggg agtctttggg attgcttcct tgttgagaga gcaaagacca    1320
gagggtggta ataacatctc tgttcaagag attgtcgaag gttaccaaag caataacttc    1380
cctttagagg ggttagccgt agatgtggat atgcaacaag atttgcgcgt gttcaccacg    1440
aagattgaat tttggacggc aaataaggta ggcaccgggg gagactcgaa taacaagtcg    1500
gtgtttgaat gggcacatga caaaggcctt gtatgtcaga cgaatgttac ttgcttcttg    1560
agaaacgaca acggcggggc agattacgaa gtcaatcaga cattgaggga aagggtttg    1620
tacacgaaga tgactcact gacgaacact aacttcggaa ctaccaacga cgggccgagc    1680
gatgcgtaca ttgacatct ggactatggt ggcgagggga attgtgatgc acttttccca    1740
gactggggtc gaccgggtgt ggctgaatgg tggggtgata actacagcaa gctcttcaaa    1800
attggtctgg atttcgtctg gcaagacatg acagttccag ctatgatgcc acacaaagtt    1860
ggcgacgcag tcgatacgag atcaccttac ggctggccga atgagaatga tccttcgaac    1920
ggacgataca attggaaatc ttaccatcca caagttctcg taactgatat gcgatatgag    1980
aatcatggaa gggaaccgat gttcactcaa cgcaatatgc atgcgtacac actctgtgaa    2040
tctacgagga aggaagggat tgttgcaaat gcagacactc taacgaagtt ccgccgcagt    2100
tatattatca gtcgtggagg ttacattggc aaccagcatt ttggaggaat gtgggttgga    2160
gacaactctt cctcccaaag ataccctcaa atgatgatcg cgaacatcgt caacatgaac    2220
atgtcttgcc ttccactagt tgggtccgac attggaggtt ttacttcgta tgatggacga    2280
aacgtgtgtc ccggggatct aatggtaaga ttcgtgcagg cgggttgctt actaccgtgg    2340
ttcagaaacc actatggtag gttggtcgag ggcaagcaag agggaaaata ctatcaagaa    2400
```

```
ctgtacatgt acaaggacga gatggctaca ttgagaaaat tcattgaatt ccgttaccgc    2460
tggcaggagg tgttgtacac tgctatgtac cagaatgcgg ctttcgggaa accgattatc    2520
aaggcagctt ccatgtacga caacgacaga aacgttcgcg gcgcacagga tgaccacttc    2580
cttctcggcg gacacgatgg atatcgtatt ttgtgtgcac ctgttgtgtg ggagaataca    2640
accagtcgcg atctgtactt gcctgtgctg accaaatggt acaaattcgg ccctgactat    2700
gacaccaagc gcctggattc tgcgttggat ggagggcaga tgattaagaa ctattctgtg    2760
ccacaaagcg actctccgat atttgtgagg aaggagcta ttctccctac ccgctacacg     2820
ttggacggtt cgaacaagtc aatgaacacg tacacagaca aagacccgtt ggtgtttgag    2880
gtattccctc ttggaaacaa ccgtgccgac ggtatgtgtt atcttgatga tggcggtatt    2940
actacagatg ctgaggacca tggcaaattc tctgttatca atgtcgaagc cttacggaaa    3000
ggtgttacga cgacgatcaa gtttgcgtat gacacttatc aatacgtatt tgatggtcca    3060
ttctacgttc gaatccgtaa tcttacgact gcatcaaaaa ttaacgtgtc ttctggagcg    3120
ggtgaagagg acatgacacc gacctctgcg aactcgaggg cagctttgtt cagtgatgga    3180
ggtgttggag aatactgggc tgacaatgat acgtcttctc tgtggatgaa gttgccaaac    3240
ctggttctgc aagacgctgt gattaccatt acgtag                              3276

<210> SEQ ID NO 9
<211> LENGTH: 3201
<212> TYPE: DNA
<213> ORGANISM: Unknown
<220> FEATURE:
<223> OTHER INFORMATION: fungus sp. or fungus infected gracilariopsis
      sp.

<400> SEQUENCE: 9
atggcaggat tttctgatcc tctcaacttt tgcaaagcag aagactacta cagtgttgcg      60
ctagactgga agggccctca aaaaatcatt ggagtagaca ctactcctcc aaagagcacc     120
aagttcccca aaaactggca tggagtgaac ttgagattcg atgatgggac tttaggtgtg     180
gttcagttca ttaggccgtg cgtttggagg gttagatacg accctggttt caagacctct     240
gacgagtatg gtgatgagaa tacgaggaca attgtgcaag attatatgag tactctgagt     300
aataaattgg atacttatag aggtcttacg tgggaaacca agtgtgagga ttcgggagat     360
ttctttacct tctcatccaa ggtcaccgcc gttgaaaaat ccgagcggac ccgcaacaag     420
gtcggcgatg gcctcagaat tcacctatgg aaaagcccct tccgcatcca agtagtgcgc     480
accttgaccc ctttgaagga tccttacccc attccaaatg tagccgcagc cgaagcccgt     540
gtgtccgaca aggtcgtttg gcaaacgtct cccaagacat tcagaaagaa cctgcatccg     600
caacacaaga tgctaaagga tacagttctt gacattgtca aacctggaca tggcgagtat     660
gtggggtggg gagagatggg aggtatccag tttatgaagg agccaacatt catgaactat     720
tttaacttcg acaatatgca ataccagcaa gtctatgccc aaggtgctct cgattctcgc     780
gagccactgt accactcgga tcccttctat cttgatgtga actccaaccc ggagcacaag     840
aatatcacgg caacctttat cgataactac tctcaaattg ccatcgactt tggaaagacc     900
aactcaggct acatcaagct gggaaccagg tatggtggta tcgattgtta cggtatcagt     960
gcggatacgg tcccggaaat tgtacgactt tatacaggtc ttgttggacg ttcaaagttg    1020
aagcccagat atattctcgg ggcccatcaa gcctgttatg gataccaaca ggaaagtgac    1080
ttgtattctg tggtccagca gtaccgtgac tgtaaatttc cacttgacgg gattcacgtc    1140
```

-continued

```
gatgtcgatg ttcaggacgg cttcagaact ttcaccacca acccacacac tttccctaac      1200
cccaaagaga tgtttactaa cttgaggaat aatggaatca agtgctccac caatatcact      1260
cctgttatca gcattaacaa cagagagggt ggatacagta ccctccttga gggagttgac      1320
aaaaaatact ttatcatgga cgacagatat accgagggaa caagtgggaa tgcgaaggat      1380
gttcggtaca tgtactacgg tggtggtaat aaggttgagg tcgatcctaa tgatgttaat      1440
ggtcggccag actttaaaga caactatgac ttccccgcga acttcaacag caaacaatac      1500
ccctatcatg tggtgtgag ctacggttat gggaacggta gtgcaggttt ttacccggac       1560
ctcaacagaa aggaggttcg tatctggtgg ggaatgcagt acaagtatct cttcgatatg      1620
ggactggaat ttgtgtggca agacatgact accccagcaa tccacacatc atatggagac      1680
atgaaagggt tgcccacccg tctactcgtc acctcagact ccgtcaccaa tgcctctgag      1740
aaaaagctcg caattgaaac ttgggctctc tactcctaca atctccacaa agcaacttgg      1800
catggtctta gtcgtctcga atctcgtaag aacaaacgaa acttcatcct cgggcgtgga      1860
agttatgccg gagcctatcg ttttgctggt ctctggactg gggataatgc aagtaactgg      1920
gaattctgga agatatcggt ctctcaagtt cttttctctgg gcctcaatgg tgtgtgcatc     1980
gcggggtctg atacgggtgg ttttgaaccc taccgtgatg caaatggggt cgaggagaaa      2040
tactgtagcc cagagctact catcaggtgg tatactggtt cattcctctt gccgtggctc      2100
aggaaccatt atgtcaaaaa ggacaggaaa tggttccagg aaccatactc gtaccccaag      2160
catcttgaaa cccatccaga actcgcagac caagcatggc tctataaatc cgttttggag      2220
atctgtaggt actatgtgga gcttagatac tccctcatcc aactacttta cgactgcatg      2280
tttcaaaacg tagtcgacgg tatgccaatc accagatcta tgctcttgac cgatactgag      2340
gataccacct tcttcaacga gagccaaaag ttcctcgaca accaatatat ggctggtgac      2400
gacattcttg ttgcacccat cctccacagt cgcaaagaaa ttccaggcga aaacagagat      2460
gtctatctcc ctctttacca cacctggtac ccctcaaatt tgagaccatg ggacgatcaa      2520
ggagtcgctt tggggaatcc tgtcgaaggt ggtagtgtca tcaattatac tgctaggatt      2580
gttgcacccg aggattataa tctcttccac agcgtggtac cagtctacgt tagagagggt      2640
gccatcatcc cgcaaatcga agtacgccaa tggactggcc aggggggagc caaccgcatc      2700
aagttcaaca tctaccctgg aaaggataag gagtactgta cctatcttga tgatggtgtt      2760
agccgtgata gtgcgccgga agacctccca cagtacaaag agacccacga acagtcgaag      2820
gttgaaggcg cggaaatcgc aaagcagatt ggaaagaaga cgggttacaa catctcagga      2880
accgacccag aagcaaaggg ttataccgcc aaagttgctg tcacacaaac gtcaaaagac      2940
aagacgcgta ctgtcactat tgagccaaaa cacaatggat acgacccttc caaagaggtg      3000
ggtgattatt ataccatcat tctttggtac gcaccaggtt tcgatggcag catcgtcgat      3060
gtgagcaaga cgactgtgaa tgttgagggt ggggtggagc accaagtta taagaactcc       3120 gatttacata cggttgttat cgacgtgaag gaggtgatcg gtaccacaaa gagcgtcaag      3180
atcacatgta ctgccgctta a                                                3201
```

<210> SEQ ID NO 10
<211> LENGTH: 3213
<212> TYPE: DNA
<213> ORGANISM: Unknown
<220> FEATURE:
<223> OTHER INFORMATION: fungus sp. or fungus infected gracilariopsis
sp.

<400> SEQUENCE: 10

```
atggcaggat tatccgaccc tctcaatttc tgcaaagcag aggactacta cgctgctgcc      60
aaaggctgga gtggccctca gaagatcatt cgctatgacc agacccctcc tcagggtaca     120
aaagatccga aaagctggca tgcggtaaac cttcctttcg atgacgggac tatgtgtgta     180
gtgcaattcg tcagaccctg tgtttggagg gttagatatg accccagtgt caagacttct     240
gatgagtacg gcgatgagaa tacgaggact attgtacaag actacatgac tactctggtt     300
ggaaacttgg acattttcag aggtcttacg tgggtttcta cgttggagga ttcgggcgag     360
tactacacct tcaagtccga agtcactgcc gtggacgaaa ccgaacggac tcgaaacaag     420
gtcggcgacg gcctcaagat ttacctatgg aaaaatccct ttcgcatcca ggtagtgcgt     480
ctcttgaccc ccctggtgga cccttttccc attcccaacg tagccaatgc cacagcccgt     540
gtggccgaca aggttgtttg gcagacgtcc ccgaagacgt tcaggaaaaa cttgcatccg     600
cagcataaga tgttgaagga tacagttctt gatattatca agccggggca cggagagtat     660
gtgggttggg gagagatggg aggcatcgag tttatgaagg agccaacatt catgaattat     720
ttcaactttg acaatatgca atatcagcag gtctatgcac aaggcgctct tgatagtcgt     780
gagccgttgt atcactctga tcccttctat ctcgacgtga actccaaccc agagcacaag     840
aacattacgg caacctttat cgataactac tctcagattg ccatcgactt tgggaagacc     900
aactcaggct acatcaagct gggtaccagg tatggcggta tcgattgtta cggtatcagc     960
gcggatacgg tcccggagat tgtgcgactt tatactggac ttgttgggcg ttcgaagttg    1020
aagcccaggt atattctcgg agcccaccaa gcttgttatg gataccagca ggaaagtgac    1080
ttgcatgctg ttgttcagca gtaccgtgac accaagtttc gcttgatgg gttgcatgtc     1140
gatgtcgact tcaggacaa tttcagaacg tttaccacta cccgattac gttccctaat      1200
cccaaagaaa tgtttaccaa tctaaggaac aatggaatca gtgttccac caacatcacc     1260
cctgttatca gtatcagaga tcgcccgaat gggtacagta ccctcaatga gggatatgat    1320
aaaaagtact tcatcatgga tgacagatat accgagggga caagtgggga cccgcaaaat    1380
gttcgatact cttttttacgg cggtgggaac ccggttgagg ttaaccctaa tgatgtttgg    1440
gctcggccag actttggaga caattatgac ttccctacga acttcaactg caaagactac    1500
ccctatcatg gtggtgtgag ttacggatat gggaatggca ctccaggtta ctaccctgac    1560
cttaacagag aggaggttcg tatctggtgg ggattgcagt acgagtatct cttcaatatg    1620
ggactagagt ttgtatggca agatatgaca accccagcga tccattcatc atatggagac    1680
atgaaagggt tgcccacccg tctgctcgtc accgccgact cagttaccaa tgcctctgag    1740
aaaaagctcg caattgaaag ttgggctctt tactcctaca acctccataa agcaaccttc    1800
cacggtcttg tcgtcttga gtctcgtaag aacaaacgta acttcatcct cggacgtggt    1860
agttacgccg gtgcctatcg ttttgctggt ctctggactg gagataacgc aagtacgtgg    1920
gaattctgga agatttcggt ctcccaagtt ctttctctag gtctcaatgg tgtgtgtata    1980
gcggggtctg atacgggtgg ttttgagccc gcacgtactg agattgggga ggagaaatat    2040
tgcagtccgg agctactcat caggtggtat actggatcat ccttttgcc atggcttaga     2100
aaccactacg tcaagaagga caggaaatgg ttccaggaac catacgcgta ccccaagcat    2160
cttgaaaccc atccagagct cgcagatcaa gcatggcttt acaaatctgt tctagaaatt    2220
tgcagatact gggtagagct aagatattcc ctcatccagc tccttacga ctgcatgttc     2280
```

-continued

```
caaaacgtgg tcgatggtat gccacttgcc agatctatgc tcttgaccga tactgaggat    2340
acgaccttct tcaatgagag ccaaaagttc ctcgataacc aatatatggc tggtgacgac    2400
atccttgtag cacccatcct ccacagccgt aacgaggttc cgggagagaa cagagatgtc    2460
tatctccctc tattccacac ctggtacccc tcaaacttga accgtggga cgatcaggga    2520 gtcgctttag ggaatcctgt cgaaggtggc agcgttatca actacactgc caggattgtt    2580
gccccagagg attataatct cttccacaac gtggtgccgg tctacatcag agagggtgcc    2640
atcattccgc aaattcaggt acgccagtgg attggcgaag agggcctaa tcccatcaag    2700 ttcaatatct accctggaaa ggacaaggag tatgtgacgt accttgatga tggtgttagc    2760
cgcgatagtg caccagatga cctcccgcag taccgcgagg cctatgagca agcgaaggtc    2820
gaaggcaaag acgtccagaa gcaacttgcg gtcattcaag gaataagac taatgacttc    2880 tccgcctccg ggattgataa ggaggcaaag ggttatcacc gcaaagtttc tatcaaacag    2940
gagtcaaaag acaagacccg tactgtcacc attgagccaa acacaacgg atacgacccc    3000 tctaaggaag ttggtaatta ttataccatc attctttggt acgcaccggg ctttgacggc    3060
agcatcgtcg atgtgagcca ggcgaccgtg aacatcgagg gcgggtgga atgcgaaatt    3120 ttcaagaaca ccggcttgca tacggttgta gtcaacgtga agaggtgat cggtaccaca    3180 aagtccgtca agatcacttg cactaccgct tag                                3213
```

<210> SEQ ID NO 11
<211> LENGTH: 3279
<212> TYPE: DNA
<213> ORGANISM: Unknown
<220> FEATURE:
<223> OTHER INFORMATION: fungus sp. or fungus infected gracilariopsis sp.

<400> SEQUENCE: 11

```
atgtttccta ccctgacctt catagcgccc agcgcgctgg ccgccagcac ctttgtgggc      60
gcggatatcc gatcgggcat tcgcattcaa tccgctcttc cggccgtgcg caacgctgtg     120
cgcaggagca acattacaa tgtatccatg accgcattgt ctgacaagca accgctatc      180 agtattggcc ctgacaatcc ggacggtatc aactaccaaa actacgatta catccctgta     240
gcgggcttta cgcccctctc caacaccaac tggtatgctg ccggctcttc cactccgggc     300
ggcatcaccg actggaccgc taccatgaat gtcaaattcg accgcattga caatccgtcg     360
tactccaata accatcctgt tcagattcag gtcacgtcgt acaacaacaa cagcttcagg     420
attcgcttca accctgatgg ccccattcgt gacgtctctc gaggacctat cctgaaacag     480
caactcactt ggattcgaaa ccaggagctg gcgcagggat gtaatccgaa catgagcttc     540
tctcctgaag gtttttttgtc ttttgaaacc aaagacctaa acgttataat ctacggcaac     600
tgcaagatga gagtcacgaa gaaggatggc tacctcgtca tggagaatga cgagtgcaac     660
tcgcaatcag atggcaataa gtgtagagga ttgatgtacg ttgaccggct atacggtaat     720
gctattgctt ccgtacaaac gaattttcac aaagacactt ctcggaacga gaaattctat     780
ggtgcaggtg aagtcaactg tcgctatgag gagcagggta aggcgccgac ttatgttcta     840
gaacgctctg gactcgccat gaccaattac aattacgaca acttgaacta caaccaacca     900
gacgtcgttc ctccaggtta tcccgaccat cccaactact acattccaat gtactacgca     960
gcaccgtggt tggtcgttca gggatgcgcg gggacatcga agcaatactc gtacggttgg    1020
tttatggaca atgtctctca gtcgtacatg aacactggag atacggcgtg gaactgcgga    1080
```

```
caggaaaacc tggcatacat gggcgcgcaa tacgggccat ttgatcagca ctttgtgtat   1140
ggtgatggag atggccttga agatgtcgtc aaagcgttct cctttcttca aggaaaggag   1200
ttcgaagaca aaaaactcaa caagcgttct gtaatgcctc cgaagtacgt gtttggtttc   1260
ttccagggtg ttttcggtgc actttcactg ttgaagcaga atctgcctgc cggagagaac   1320
aacatctcag tgcaagagat tgtggagggt taccaggata cgactaccc ctttgaaggg    1380 ctcgcggtag atgttgatat gcaagatgat ctgcgagtgt ttactaccaa accagaatat   1440
tggtcggcaa acatggtagg cgaaggcggt gatcctaata acagatcagt ctttgaatgg   1500
gcacatgaca ggggccttgt ctgtcagacg aacgtaactt gcttcttgag gaacgataac   1560
agtgggaaac catacgaagt gaatcagaca ttgagggaga acagttgta tacgaagaat    1620 gattccttga acaacaccga ttttggaact acctcggatg gcctggcga tgcgtacatt    1680 ggacatttgg actatggtgg tggagtggag tgtgatgcaa tcttcccaga ctggggtcga   1740
ccagacgtgc tcaatggtg gggagaaaac tacaagaagc tgttcagcat tggtctcgat    1800
ttcgtgtggc aggatatgac ggtacctgcg atgatgccgc accgactcgg tgatgctgtc   1860
aacaaaaatt ccgtagttc ggcgccgggc tggccgaatg agaacgatcc atccaacgga    1920
cgatacaact ggaaatctta tcatccgcaa gtgctcgtga ccgacatgcg ctatggtgca   1980
gagtatggaa gggaaccgat ggtgtctcaa cgcaacattc acgcctacac tctttgtgaa   2040
tctaccagac gggagggaat tgtgggaaac gcagacagtt tgaccaagtt ccgccgcagt   2100
tacatcatca gtcgaggagg ttacatcggt aaccagcatt tcggagggat gtgggttggg   2160
gacaacagtg ccacagaatc ctacctccaa atgatgttgg cgaacattat caacatgaat   2220
atgtcgtgcc tcccgctagt tggctctgat attggcgggt tcacccagta caatgatgcg   2280
ggcgacccaa cccccgagga tttgatggta agattcgtgc aggctggctg tctgctaccg   2340
tggttcagaa accactatga caggtggatt gagtccaaga agcacgggaa gaaataccag   2400
gagttataca tgtacccggg gcaaaaggat acgttgaaga agttcgttga attccgctac   2460
cgctggcagg aggttttgta cacagccatg taccaaaatg ctaccactgg agagccgatc   2520
atcaaggcgg cgcccatgta caacaacgac gtcaacgtgt ataaatcgca gaatgatcat   2580
ttccttctcg gtggacatga cggctatcgt attctctgcg cacctgttgt gcgcgaaaat   2640
gcgacaagtc gcgaagtgta cctgcctgtg tatagcaagt ggttcaaatt cggaccggac   2700
tttgacacta agcccttgga aaatgagatt caaggaggtc agacgcttta taattacgct   2760
gcaccgctga acgattcgcc gatatttgtg agggaaggga ctattcttcc gacacggtac   2820
acgctggacg tgtgaacaa atctatcaac acgtacacag acaatgatcc gcttgtatt    2880 gagctgttcc ctctcgaaaa caaccaggcg catggcttgt tctatcatga tgatggcggt   2940
gtcaccacca acgctgaaga ctttggcaag tattctgtga tcagtgtgaa ggccgcgcag   3000
gaaggttctc aaatgagtgt caagtttgac aatgaagttt atgaacacca atggggagca   3060
tcgttctatg ttcgtgttcg taatatgggt gctccgtcta acatcaacgt atcttctcag   3120
attggtcaac aggacatgca acagagctcc gtgagttcca gggcgcaaat gttcactagt   3180
gctaacgatg gcgagtactg ggttgaccag agcacgaact cgttgtggct caagttgcct   3240
ggtgcagtta tccaagacgc tgcgatcact gttcgttga                          3279
```

<210> SEQ ID NO 12
<211> LENGTH: 1712
<212> TYPE: DNA
<213> ORGANISM: Unknown

-continued

```
<220> FEATURE:
<223> OTHER INFORMATION: fungus sp. or fungus infected gracilariopsis
      sp.

<400> SEQUENCE: 12
atgacaaact ataattatga caatttgaac tacaatcaac cggacctcat cccacctggc      60
catgattcag atcctgacta ctatattccg atgtactttg cggcaccatg ggtgatcgca     120
catggatatc gtggcaccag cgaccagtac tcttatggat ggttttttgga caatgtatcc    180 cagtcctaca caaacactgg cgatgatgca tgggctggtc agaaggattt ggcgtacatg    240
ggggcacaat gtgggccttt cgatcaacat tttgtgtatg aggctggaga tggacttgaa    300
gacgttgtga ccgcattctc ttatttgcaa ggcaaggaat atgagaacca gggactgaat    360
atacgttctg caatgcctcc gaagtacgtt ttcggatttt tccaaggcgt attcggagcc    420
acatcgctgc taagggacaa cttacctgcc ggcgagaaca acgtctcttt ggaagaaatt    480
gttgaaggat atcaaaatca gaacgtgcca tttgaaggtc ttgctgtgga tgttgatatg    540
caagatgact tgagagtgtt cactacgaga ccagcgtttt ggacggcaaa caaggtgggg    600
gaaggcggtg atccaaacaa caagtcagtg tttgagtggg cacatgacag gggccttgtc    660
tgccagacga atgtaacttg cttcttgaag aacgagaaaa atccttacga agtgaatcag    720
tcattgaggg agaagcagtt gtatacgaag agtgattcct tggacaacat tgattttgga    780
actactccag atgggcctag cgatgcgtac attggacact tagactacgg tggtggtgtg    840
gagtgtgatg cactattccc agactggggt cgaccagacg tggctcaatg gtggggcgat    900
aactacaaga aactattcag cattggtctc gatttcgtct ggcaagatat gacggtacct    960
gcgatgatgc cgcaccgact cggtgaccct gtcggcacaa attccggtga gacggcgccg   1020
ggctggccga atgataagga tccatccaac ggacgataca attggaagtc ttaccatccg   1080
caagtgctcg tgactgacat gaggtatgac gattacggaa gagatcccat tgttacgcaa   1140
cgcaatctcc atgcctacac tctttgtgag tctactagga gggaaggcat tgttggaaac   1200
gcagatagtc tgacgaagtt ccgccgcagc tatattatca gtcgtggagg ctacatcggt   1260
aatcagcact ttggtgggat gtgggtagga gacaactctt ctacggaaga ctacctcgca   1320
atgatggtta tcaacgttat caacatgaac atgtccggtg tcccgctcgt tggttccgat   1380
attggaggtt tcacggagca tgacaagaga accccttgca caccggactt gatgatgaga   1440
tttgtgcagg ctggatgctt gctaccgtgg ttcaggaacc actacgatag gtggatcgag   1500
agcaagaaac acggaaagaa ctaccaagag ttgtacatgt accgcgacca cttgacgcc    1560 ttgagaagtt ttgtggaact ccgctatcgc tggcaggaag tgttatacac agccatgtat   1620
cagaatgctt tgaacgggaa gccgatcatc aaaacggtct ccatgtacaa caacgatatg   1680
aacgtcaaag atgctcagaa tgaccacttc ct                                 1712
```